(12) United States Patent
Ellingson et al.

(10) Patent No.: US 10,973,433 B2
(45) Date of Patent: Apr. 13, 2021

(54) LEAKAGE CORRECTION FOR DSC-PERFUSION MRI BY ACCOUNTING FOR BIDIRECTIONAL CONTRAST AGENT EXCHANGE

(71) Applicant: The Regents of the University of California, Oakland, CA (US)

(72) Inventors: Benjamin Ellingson, Los Angeles, CA (US); Kevin Leu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 350 days.

(21) Appl. No.: 15/754,237

(22) PCT Filed: Aug. 30, 2016

(86) PCT No.: PCT/US2016/049486
§ 371 (c)(1),
(2) Date: Feb. 21, 2018

(87) PCT Pub. No.: WO2017/040523
PCT Pub. Date: Mar. 9, 2017

(65) Prior Publication Data
US 2018/0249925 A1    Sep. 6, 2018

Related U.S. Application Data

(60) Provisional application No. 62/211,820, filed on Aug. 30, 2015.

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/0042* (2013.01); *G01R 33/5601* (2013.01);
(Continued)

(58) Field of Classification Search
None
See application file for complete search history.

(56) References Cited

U.S. PATENT DOCUMENTS 7,567,832 B2    7/2009    Schmainda
7,643,864 B2    1/2010    Elgort
(Continued)

FOREIGN PATENT DOCUMENTS

WO    2000072037    11/2000
WO    2012149401    11/2012

OTHER PUBLICATIONS

Boxerman et al. "Relative Cerebral Blood Volume Maps Corrected for Contrast Agent Extravasation Significantly Correlate with Glioma Tumor Grade, Whereas Uncorrected Maps Do Not". AJNR Am J Neuroradiol 27:859-67. Apr 2006. (Year: 2006).*

(Continued)

*Primary Examiner* — Jeffrey G Hoekstra
*Assistant Examiner* — Jillian K. McGough
(74) *Attorney, Agent, or Firm* — Quarles & Brady LLP

(57) ABSTRACT

A post-processing leakage correction system and method that accounts for bidirectional contrast agent transport between the intravascular and interstitial spaces that commonly occurs in angiogenic high-grade gliomas without a substantial increase in post-processing computation time.

20 Claims, 15 Drawing Sheets

(51) Int. Cl.
 G01R 33/56 (2006.01)
 G01R 33/563 (2006.01)
(52) U.S. Cl.
 CPC . *G01R 33/56308* (2013.01); *G01R 33/56366* (2013.01); *G01R 33/5602* (2013.01)

(56) References Cited

U.S. PATENT DOCUMENTS

| | | | |
|---|---|---|---|
| 8,670,602 B2 | 3/2014 | Schmainda et al. | |
| 2013/0329973 A1* | 12/2013 | Cao | A61B 5/0033 382/128 |
| 2014/0039300 A1* | 2/2014 | Gjesdal | A61B 5/055 600/420 |

OTHER PUBLICATIONS

Cox, Robert. "AFNI: Software for Analysis and Visualization of Functional Magnetic Resonance Neuroimages". Computers and Biomedical Research 29, 162-173 (1996). (Year: 1996).*
Schmiedeskamp et al."Simultaneous perfusion and permeability measurements using combined spin- and gradient-echo MRI". Journal of Cerebral Blood Flow & Metabolism (2013), 732-743. (Year: 2013).*
Leu et al. "Improved Leakage Correction for Single-Echo Dynamic Susceptibility Contrast Perfusion MRI Estimates of Relative Cerebral Blood Volume in High-Grade Gliomas by Accounting for Bidirectional Contrast Agent Exchange". American Journal of Neuroradiology Aug. 2016, 37 (8) 1440-1446; (Year: 2016).*
Larsson et al. "Measurement of Brain Perfusion, Blood Volume, and Blood-Brain Barrier Permeability, Using Dynamic Contrast-Enhanced T1-Weighted MRI at 3 Tesla". Magnetic Resonance in Medicine 62:1270-1281 (2009). (Year: 2009).*
Tofts et al., "Measurement of the Blood-Brain Barrier Permeability and Leakage Space Using Dynamic MR Imaging. 1. Fundamental Concepts", 1991, Magnetic Resonance in Medicine 17, p. 357-367. (Year: 1991).*
Aronen HJ, et al. Cerebral blood volume maps of gliomas: comparison with tumor grade and histologic findings. Radiology 1994;191:41-51.
Bjornerud A, et al. T1- and T2*-dominant extravasation correction in DSC-MRI, part I: theoretical considerations and implications for assessment of tumor hemodynamic properties. J Cereb Blood Flow Metab 2011;31:2041-53.
Boxerman JL, et al. Longitudinal DSCMRI for distinguishing tumor recurrence from pseudoprogression in patients with a high-grade glioma. Am J Clin Oncol Nov. 26, 2014.
Boxerman JL, et al. The role of preload and leakage correction in gadolinium-based cerebral blood volume estimation determined by comparison withMIONas a criterion standard. AJNR Am J Neuroradiol 2012;33:1081-87.
Boxerman JL, Schmainda KM, Weisskoff RM. Relative cerebral blood volume maps corrected for contrast agent extravasation significantly correlate with glioma tumor grade, whereas uncorrected maps do not. AJNR Am J Neuroradiol 2006;27:859-867.
Brem S, et al. Tumor angiogenesis: a quantitative method for histologic grading. J Natl Cancer Inst 1972;48:347-356.
Cha S, et al. Intracranial mass lesions: dynamic contrast-enhanced susceptibility-weighted echo-planar perfusion MR imaging. Radiology 2002;223:11-29.
Danchaivijitr N, et al. Low-grade gliomas: do changes in rCBV measurements at longitudinal perfusionweighted MR imaging predict malignant transformation? Radiology 2008;247:170-78.
Donahue KM, et al. Utility of simultaneously acquired gradient-echo and spin-echo cerebral blood volume and morphology maps in brain tumor patients. Magn Reson Med 2000;43:845-53.
Ellingson BM, et al. Quantitative volumetric analysis of conventional MRI response in recurrent glioblastoma treated with bevacizumab. Neurooncology 2011;13:401-409.
Essig M, et al. Perfusion MRI: the five most frequently asked clinical questions. AJR Am J Roentgenol 2013;201:W495-510.
Fananapazir G, et al. Vascular artifact mimicking thrombosis on MR imaging using ferumoxytol as a contrast agent in abdominal vascular assessment. J Vasc Interv Radiol 2014;25:969-976.
Farrell BT, et al. Using iron oxide nanoparticles to diagnose CNS inflammatory diseases and PCNSL. Neurology 2013; 81:256-263.
Gahramanov S, et al. Improved perfusion MR imaging assessment of intracerebral tumor blood volume and antiangiogenic therapy efficacy in a rat model with ferumoxytol. Radiology 2011;261:796-804.
Gahramanov S, et al. Diagnosis of pseudoprogression using MRI perfusion in patients with glioblastoma multiforme may predict improved survival.CNSOncol 2014;3:389-400.
Harris RJ, et al. MRI perfusion measurements calculated using advanced deconvolution techniques predict survival in recurrent glioblastoma treated with bevacizumab. J Neurooncol 2015;122:497-505.
Hu LS, et al. Optimized preload leakagecorrection methods to improve the diagnostic accuracy of dynamic susceptibility-weighted contrast-enhanced perfusion MR imaging in posttreatment gliomas. AJNR Am J Neuroradiol 2010;31:40-48.
International Search Report and Written Opinion for application PCT/US2016/049486, dated Dec. 5, 2016, 9 pages.
Johnson DR, et al. Glioblastoma survival in the United States before and during the temozolomide era. J Neurooncol 2012;107:359-364.
Kickingereder P, et al. Relative cerebral blood volume is a potential predictive imaging biomarker of bevacizumab efficacy in recurrent glioblastoma. Neurooncology 2015;17:1139-1147.
Laviolette PS, et al. Vascular change measured with independent component analysis of dynamic susceptibility contrast MRI predicts bevacizumab response in high-grade glioma. Neuroncology 2013;15:442-450.
Law M, et al. Low-grade gliomas: dynamic susceptibility-weighted contrast-enhanced perfusion MR imaging—prediction of patient clinical response. Radiology 2006;238:658-67.
Law M, et al. Glioma grading: sensitivity, specificity,and predictive values of perfusion MR imaging and proton MR spectroscopic imaging compared with conventional MR imaging. AJNR Am J Neuroradiol 2003;24:1989-98.
Leu K, et al. Hypervascular volume estimated by comparison to a large-scale cerebral blood volume (Cb v) radiographic atlas predicts survival in recurrent glioblastoma treated with bevacizumab. Neurooncology 2014;16.
Ludemann L, et al. Pharmacokinetic modeling of Gd-DTPA extravasation in brain tumors. Invest Radiol 2002;37:562-70.
Meier P, et al. On the theory of the indicator-dilution method for measurement of blood flow and volume. J Appl Physiol 1954;6:731-744.
Murase K. Efficient method for calculating kinetic parameters using T-1-weighted dynamic contrast-enhanced magnetic resonance imaging. Magn Reson Med 2004;51:858-862.
Nowosielski M, et al. Progression types after antiangiogenic therapy are related to outcome in recurrent glioblastoma. Neurology 2014;82:1684-1692.
Ostrom QT, et al. CBTRUS statistical report: primary brain and central nervous system tumors diagnosed in the United States in 2008-2012. Neurooncology 2015;17(Suppl 4):iv1-iv62.
Ostrom QT, et al. CBTRUS statistical report: primary brain and central nervous system tumors diagnosed in the United States in 2007-2011. Neurooncology 2014;16(Suppl 4):iv1-63.
Paulson ES, et al. Comparison of dynamic susceptibilityweighted contrast-enhanced MR methods: recommendations for measuring relative cerebral blood volume in brain tumors. Radiology 2008;249:601-613.
Quarles CC, et al. A theoretical framework to model DSC-MRI data acquired in the presence of contrast agent extravasation. Phys Med Biol 2009;54:5749-5766.
Quarles CC, et al. Improving the reliability of obtaining tumor hemodynamic parameters in the presence of contrast agent extravasation. Magn Reson Med 2005;53:1307-16.

(56) References Cited

OTHER PUBLICATIONS

Roberts HC, et al. Quantitative measurement of microvascular permeability in human brain tumors achieved using dynamic contrast-enhanced MR imaging: correlation with histologic grade. AJNR Am J Neuroradiol 2000;21:891-99.

Rosen BR, et al. Perfusion imaging with NMR contrast agents. Magn Reson Med 1990;14:249-265.

Schmainda KM, et al. Characterization of a firstpass gradient-echo spin-echo method to predict brain tumor grade and angiogenesis. AJNR Am J Neuroradiol 2004;25:1524-1532.

Schmainda KM, et al. Dynamic susceptibility contrast MRI measures of relative cerebral blood volume as a prognostic marker for overall survival in recurrent glioblastoma: results from the ACRIN 6677/RTOG 0625 multicenter trial. Neuro Oncol 2015;17:1148-56.

Schmiedeskamp H, et al. Simultaneous perfusion and permeability measurements using combined spin- and gradientecho MRI. J Cereb Blood Flow Metab 2013;33:732-743.

Tofts PS, et al. Measurement of the blood-brain barrier permeability and leakage space using dynamic MR imaging. 1. Fundamental concepts. Magn Reson Med 1991;17:357-367.

Villringer A, et al. Dynamic imaging with lanthanide chelates in normal brain: contrast due to magnetic susceptibility effects. Magn Reson Med 1988;6:164-74.

Weisskoff R, et al. Simultaneous blood volume and permeability mapping using a single Gdbased contrast Injection. In: Proc 2nd Annual Meeting ISMRM, San Francisco; 1994.

Wen PY, et al. Updated response assessment criteria for high-grade gliomas: response assessment in neuro-oncology working group. J Clin Oncol 2010;28:1963-1972.

\* cited by examiner

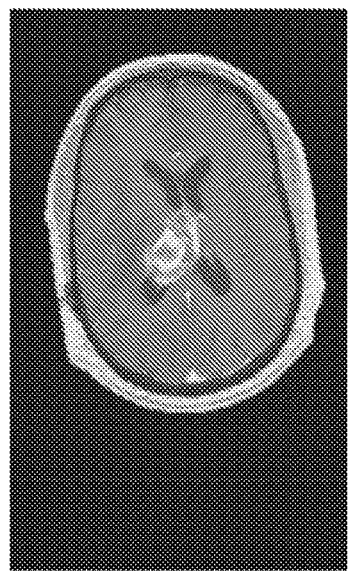 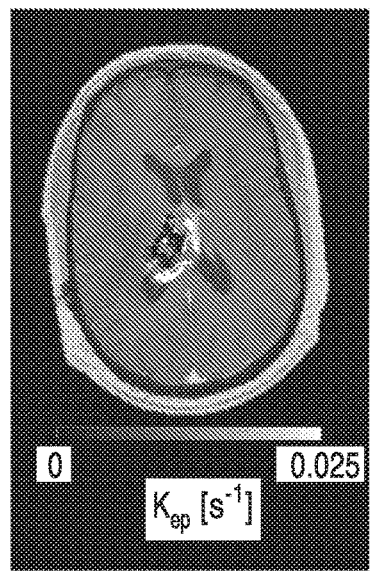 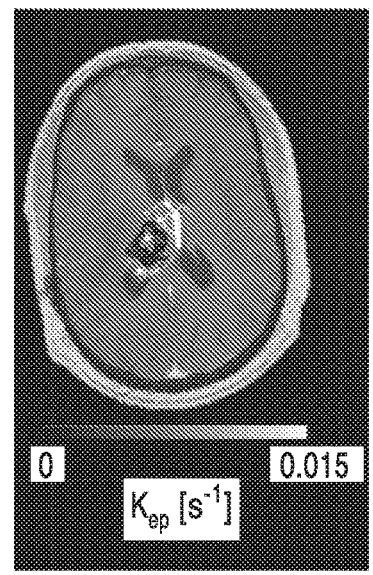
FIG. 6A  FIG. 6B  FIG. 6C
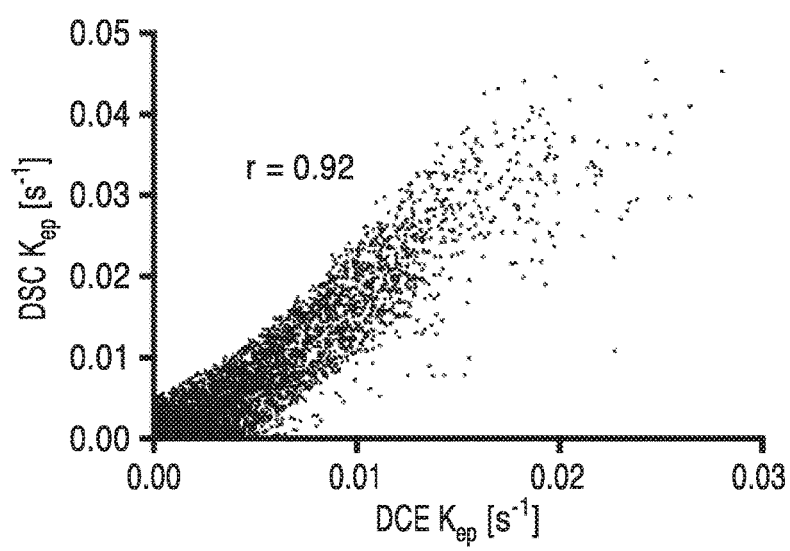
FIG. 7

LEAKAGE CORRECTION FOR DSC-PERFUSION MRI BY ACCOUNTING FOR BIDIRECTIONAL CONTRAST AGENT EXCHANGE

CROSS-REFERENCE TO RELATED APPLICATIONS

This application represents the national stage entry of PCT International Application PCT/US2016/049486 filed Aug. 30, 2016, which claims benefit of U.S. Provisional Application 62/211,820 filed Aug. 30, 2015, all of which is incorporated herein in its entirety by reference.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to medical imaging, and more particularly to dynamic susceptibility contrast magnetic resonance imaging (DSC-MRI).

2. Background Discussion

Every year in the United States, approximately 44,000 new primary brain tumors are diagnosed. Approximately 60% of these are malignant and 45% are gliomas. Malignant gliomas are the second leading cause of cancer mortality in people under the age of 35, the fourth leading cause in those under the age of 54, and kill approximately 13,000 patients per year. Glioblastoma multiforme (GBM) is a particular type of infiltrative malignant glioma that carries an abysmal prognosis. Current standard of care for GBMs includes maximal surgical resection, radiation therapy with concurrent cytotoxic chemotherapy, followed by subsequent chemotherapy. Despite recent advances in surgical procedures, radiation and chemotherapy, median survival time is still only around 14 months for GBM patients and prognosis has not changed significantly in the last 30 years. Thus, there is an urgent need for more advanced treatment strategies that complement standard antineoplastic therapies.

Anatomical MRI techniques with and without the addition of intravenous contrast agents are the current "gold standard" for detection and treatment response assessments in brain tumors. T2-weighted and T2-weighted fluid attenuated inversion recovery (FLAIR) images are used to locate regions of edema surrounding bulky tumors, but regions of edema may also harbor invading or proliferating tumor cells.

Dynamic susceptibility contrast magnetic resonance imaging (DSC-MRI) is a perfusion-weighted imaging technique based on indicator-dilution theory that uses the first-pass of a paramagnetic contrast agent to estimate cerebrovascular parameters, including relative cerebral blood volume (rCBV) and relative cerebral blood flow (rCBF).

The most common (DSC)-MRI metric in neuro-oncology is relative cerebral blood volume (rCBV), which has been used for grading gliomas, predicting low-grade to high-grade transformation, distinguishing recurrent tumor from pseudo progression, differentiating tumor regression from pseudo response, and assessing overall treatment response. Relative CBV is typically calculated by integrating the dynamic first-pass change in transverse relaxation rate ($\Delta R_2^*$) resulting from bolus injection of gadolinium-based contrast agent, which transiently causes a dose-dependent change in magnetic susceptibility of the blood. This technique mimics classic indicator-dilution theory, which assumes intravascular compartmentalization of injected contrast agent "tracer".

However, common gadolinium-based contrast agents extravasate in lesions with blood-brain barrier disruption, including malignant gliomas. The exchange of contrast agent between the intravascular and the extravascular, extracellular space, which is the objective measurement in dynamic contrast enhanced (DCE)-MRI, contaminates the desired DSC-MRI signal, depending on pulse sequence parameters and underlying tumor biology.

A popular model-based DSC-MRI leakage correction method (referred to as the Boxerman-Weisskoff model or Unidirectional-model) linearly fits measured $\Delta R_2^*(t)$ to two constant functions derived from average relaxation rate in non-enhancing tissue, one of which is permeability-weighted. Deviation from the reference function is used to derive corrected rCBV for each voxel. A limiting assumption of this approach is that contrast agent reflux from the interstitial space back to blood plasma is negligible within the time frame of DSC-MRI signal acquisition (~2 minutes).

As mentioned above, neovascularity within neoplasms tends to have elevated vascular permeability, resulting in contrast agent leakage into the extravascular, extracellular space and violation of assumptions made by the indicator-dilution theory. These "leakage effects" highly depend upon the acquisition strategy and protocol used for DSC-MRI signal acquisition. For example, DSC-MRI acquisitions with high flip angles produce more T1-weighted leakage artifacts during contrast agent extravasation, with consequent underestimation of rCBV. Conversely, T2*-weighted leakage artifacts arise with low flip angle (or even dual-echo) acquisitions, leading to overestimation rCBV.

BRIEF SUMMARY

Contrast agent extravasation through a disrupted blood-brain barrier potentiates inaccurate dynamic susceptibility contrast MRI (DSC-MRI) estimation of physiological characteristics such as relative cerebral blood volume (rCBV). An aspect of the image processing system and methods of the present description is a leakage correction model that accounts for interstitial washout rate for single-echo, gradient-echo DSC-MRI that provides significant improvement in rCBV estimates in high-grade gliomas.

The system and methods of the present description deviate from traditional model-based post-processing leakage correction techniques that assume unidirectional contrast agent extravasation, and instead account for bidirectional contrast agent exchange between intra- and extravascular spaces, herein referred to as the Bidirectional-model.

The technology described herein involves the transformation of a dynamic series of T2*-weighted magnetic resonance (MR) images acquired during injection of an MR contrast agent, into an image depicting a more accurate estimate of relative blood volume, particularly during pathological circumstances when contrast agent has leaked from the blood vessels. The raw dynamic T2*-weighted images, themselves, have very little clinical value, whereas the blood volume images generated by the technology of the present disclosure are particularly useful for the diagnosis and measurement of treatment response in human pathologies including cancer and stroke. In other words, the technology described herein transforms dynamic T2* images into blood volume images.

The Bidirectional-model shows improved AIC versus the Unidirectional-model in >50% of enhancing tumor voxels in all 21 GBMs (77%±9%; p<0.0001), and reduced ED in >50% of enhancing tumor voxels for 17/21 GBMs (62%±17%; p=0.0041). Correlation between Bidirectional-model- and DCE-derived $k_{ep}$ demonstrates a strong correlation (r=0.74±0.13). On average, enhancing tumor rCBV for the Unidirectional-model exceeded that for the Bidirectional-model by 16.6±14.0%.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 6A shows a post-contrast, T1-weighted image.

FIG. 6B shows an image of DSC-derived $k_{ep}$ and DCE-derived $k_{ep}$.

FIG. 6C shows an image of DSC-derived $k_{ep}$ and DCE-derived $k_{ep}$.

FIG. 7 shows a plot of a correlation test performed between the bidirectional model-derived rCBV and DCE-derived $K_{trans}$.

DETAILED DESCRIPTION

Figure 1:
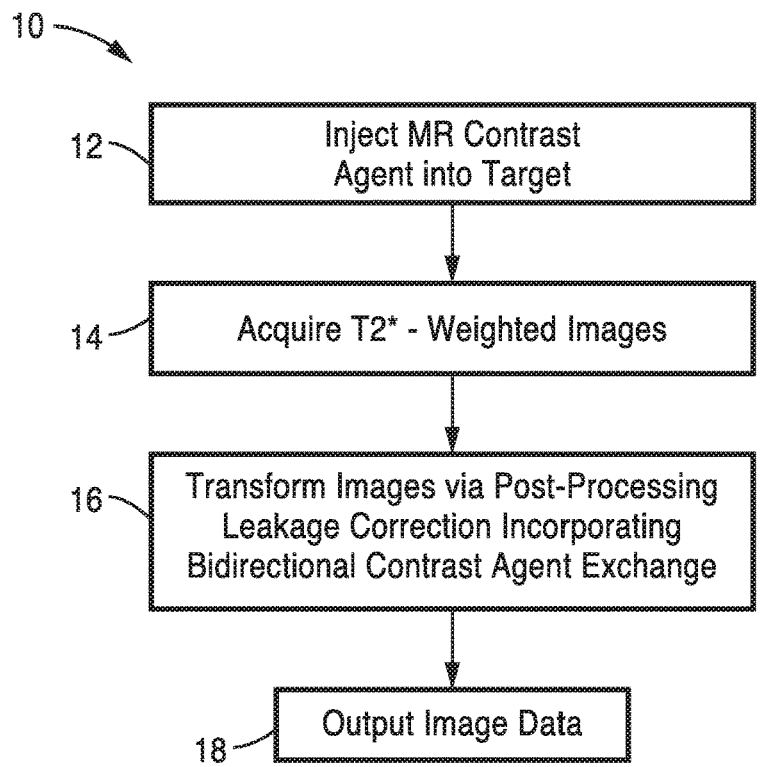
FIG. 1 shows a flow diagram of a method 10 for leakage correction during magnetic resonance imaging in accordance with the present description.

The systems and methods below detail an improved post-processing leakage correction system and method that accounts for bidirectional contrast agent transport between the intravascular and interstitial spaces that commonly occurs in angiogenic high-grade gliomas without a substantial increase in post-processing computation time. The interstitial washout term, which is previously not accounted for in traditional systems, is shown to be an important consideration in evaluating/imaging physiological characteristics (such as blood volume) in target anatomy such as arteries and brain, and even when modeling the relaxation rate changes during short image acquisitions.

The following description first provides a discussion of the underlying physics used to generate the bidirectional model used in transformation of the baseline data to account for contrast agent transport between the intravascular and interstitial spaces. Two separate studies are then detailed showing the improvements that the systems and methods provide for DSC-MRI and dynamic contrast enhanced (DCE)-MRI.

The baseline signal for gradient echo acquisitions can be described as:

$$S_0 = M_0 \cdot \frac{1 - E_1}{1 - \cos \alpha \cdot E_1} \cdot \sin \alpha \cdot E_2^*,$$

where $S_0$ is the signal amplitude, $M_0$ is the amplitude of the initial magnetization vector, $\alpha$ is the flip angle, $E_1 = e^{-TR/T_{10}}$, $E_2^* = e^{-TE/T_{20}^*}$, $T_{10}$ is the inherent pre-contrast tissue $T_1$ relaxation rate, and $T_{20}^*$ is the inherent pre-contrast tissue $T_2^*$ relaxation rate.

As a result of a bolus of contrast agent passing through the vasculature, there is a corresponding shift in T1 and T2*, yielding the following signal due to the leakage of contrast agent into the tissue:

$$S(t) = M_0 \cdot \sin \alpha \cdot \frac{1 - e^{-TR \cdot (\Delta R_1(t) + R_{10})}}{1 - \cos \alpha \cdot e^{-TR \cdot (\Delta R_1(t) + R_{10})}} \cdot e^{-TE \cdot [\Delta R_{2,P}^*(t) + \Delta R_{2,E}^*(t)]} \cdot E_2^*,$$

where TR is the repetition time, TE is the echo time, $\Delta R_1$ is the T1 shortening from contrast agent extravasation, $\Delta R_{2,P}^*$ is the intravascular susceptibility from the contrast agent, and $\Delta R_{2,E}^*$ is the susceptibility caused by contrast agent extravasation. More specifically, $$\Delta R_1(t) = r_1 C_E(t),$$

and $$\Delta R_{2,P}^*(t) + \Delta R_{2,E}^*(t) = r_2[v_E C_E(t) + v_P C_P(t)] + K_P v_P v_E |C_P(t) - C_E(t)| K_P v_P v_I C_P(t) + K_E v_E v_I C_E(t),$$

where E represents the extravascular space, I represents the intracellular space, and P represents the plasma space.

Furthermore, v represents the volume fraction, K are "calibration factors", and C represents the concentration of gadolinium:

$$K_P v_P v_E |C_P(t) - C_E(t)| = \begin{cases} K_P v_P v_E (C_P(t) - C_E(t)), & \text{if } C_P(t) > C_E(t) \\ K_P v_P v_E (C_E(t) - C_P(t)), & \text{if } C_E(t) > C_P(t). \end{cases}$$

Rearranging and substitution of the terms from the prior two equations yields:

$$\Delta R_{2,P}^*(t) = \begin{cases} [r_2 v_P + K_P v_P v_I + K_P v_P v_E] C_P(t), & \text{if } C_P(t) > C_E(t) \\ [r_2 v_P + K_P v_P v_I - K_P v_P v_E] C_P(t), & \text{if } C_E(t) > C_P(t) \end{cases} = r_{2,P}^* C_P(t)$$

$$\Delta R_{2,E}^*(t) = \begin{cases} [r_2 v_E + K_E v_E v_I - K_P v_P v_E] C_E(t), & \text{if } C_P(t) > C_E(t) \\ [r_2 v_E + K_E v_E v_I + K_P v_P v_E] C_E(t), & \text{if } C_E(t) > C_P(t) \end{cases} = r_{2,E}^* C_E(t).$$

The leakage contaminated, time-dependent change in transverse relaxation rate is defined as:

$$\Delta \tilde{R}_2^* = -\frac{1}{TE} \ln\left(\frac{S(t)}{S_0}\right),$$

where the tilde indicates that the signal has been contaminated by either T1 or T2* relaxation enhancement.

The total leakage-contaminated change in relaxation rate as a function of time can be described as the sum of the true relaxation rate plus the change due to leakage:

$$\Delta \tilde{R}_2^*(t) = \Delta R_{2,P}^*(t) + \Delta \hat{R}_2^*(t),$$

where $\Delta \hat{R}_2^*(t)$ is the change in relaxation rate due to T1 and T2* leakage.

The leakage-contaminated DSC-MRI relaxation rate-time curve of Eq. 1, $\Delta \hat{R}_2^*(t)$, equals intravascular contrast-driven transverse relaxation rate change, $\Delta R_2^*(t)$, plus $\Delta R_2^*(t)$, a tissue leakage term describing the simultaneous T1 and T2* relaxation effects resulting from gadolinium extravasation:

$$\Delta \hat{R}_2^*(t) = \qquad\qquad\qquad\qquad\qquad\qquad \text{Eq. 1}$$

$$\Delta R_2^*(t) + \Delta R_{2,E}^*(t) = \Delta R_2^*(t) + \left[r_{2,E}^* - \frac{TR}{TE} \cdot \left(\frac{E_1}{1 - E_1}\right) \cdot r_1\right] C_E(t),$$

where $E_1 = e^{-TR/T_{10}}$, $T_{10}$ is the pre-contrast tissue $T_1$, $r_1$ is the $T_1$ relaxivity of gadolinium, $C_E(t)$ is the concentration of gadolinium in the extravascular, extracellular space, and $r_{2,E}^*$ represents the $T_{2*}$ relaxation effects of gadolinium extravasation.

Using the original Tofts model to describe bidirectional contrast agent flux between the intravascular and extravascular compartments, the concentration in tissue can be characterized as:

$$C_E(t) = k_{trans} \cdot (C_p(t) * e^{-k_e p t}), \qquad\qquad \text{Eq. 2}$$

where $k_{trans}$ and $k_{ep}$ are the transfer coefficients for intra- to extravascular and extra- to intravascular contrast flux, respectively, and $C_p(t)$ is the plasma contrast concentration.

By defining the arterial input function and the "true" $\Delta R_2^*$ using the whole brain average:

$$C_p(t) = k \cdot \Delta \overline{R}_2^*(t), \qquad\qquad \text{Eq. 3}$$

and $$\Delta R_2^*(t) = K_1 \cdot \Delta \overline{R}_2^*(t), \qquad\qquad \text{Eq. 4}$$

where $\Delta \overline{R}_2^*(t)$ is the whole brain average signal.

Combining Eq. 1 through Eq. 4 yields:

$$\Delta \hat{R}_2^*(t) = K_1 \cdot \Delta \overline{R}_2^*(t) - K_2 \int_0^t \Delta \overline{R}_2^*(T) \cdot e^{-k_{ep}(t-T)} dT, \quad \text{Eq. 5}$$

where:

$$K_2 = \left[ r_{2,E}^* - \frac{TR}{TE} \cdot \left( \frac{E_1}{1-E_1} \right) \cdot r_1 \right] \cdot k_{trans} \cdot k. \quad \text{Eq. 6}$$

$K_1$, $K_2$, and $k_{ep}$ (units of sec$^{-1}$) are the free parameters of Eq. 5. In general, $K_1$ depends on CBV, vessel size, and other physiologic factors, while $K_2$ is related to vascular permeability. Substituting $k_{ep}=0$, which occurs with no backflow of extravasated contrast agent, yields the original Unidirectional leakage correction algorithm, where $K_1$ and $K_2$ are solved by linear least squares fit to $\Delta \hat{R}_2^*(t)$. For the Bidirectional-model correction method, a linear least squares fit to $K_1$, $K_2$, and $k_{ep}$ can be employed using the methodology of Murase, as described by the Eq. 7:

$$\Delta \hat{R}_2^*(t) = (K_2 + k_{ep} \cdot K_1) \int_0^t \Delta \overline{R}_2^*(\tau) d\tau - k_{ep} \int_0^t \Delta \hat{R}_2^*(\tau) d\tau + K_1 \cdot \Delta \overline{R}_2^*(t). \quad \text{Eq. 7}$$

Integrating the corrected relaxation rate-time curve yields the leakage-corrected rCBV in Eq. 8:

$$rCBV_{corr} = rCBV + K_2 \int_0^T \int_0^t \Delta \overline{R}_2^*(\tau) \cdot e^{-k_{ep}(t-\tau)} d\tau dt \quad \text{Eq. 8}$$

FIG. 1 shows a flow diagram of a method 10 for leakage correction during magnetic resonance imaging in accordance with the present description. First, a Magnetic Resonance (MR) contrast agent is injected or otherwise delivered into a patient at step 12 for delivery to a biological target anatomy of interest (e.g. brain).

Next at step 14, a dynamic series of T2*-weighted MR images of the target anatomy are acquired delivery of the MR contrast agent to the target anatomy.

At step 16, the T2*-weighted MR images, or baseline images, are transformed into the output image data 18 (e.g. images comprising data or maps of corrected relative cerebral blood volume (rCBV) and/or relative cerebral blood flow (rCBF)) of the target via the bidirectional leakage correction algorithm of the present description.

Figure 2:
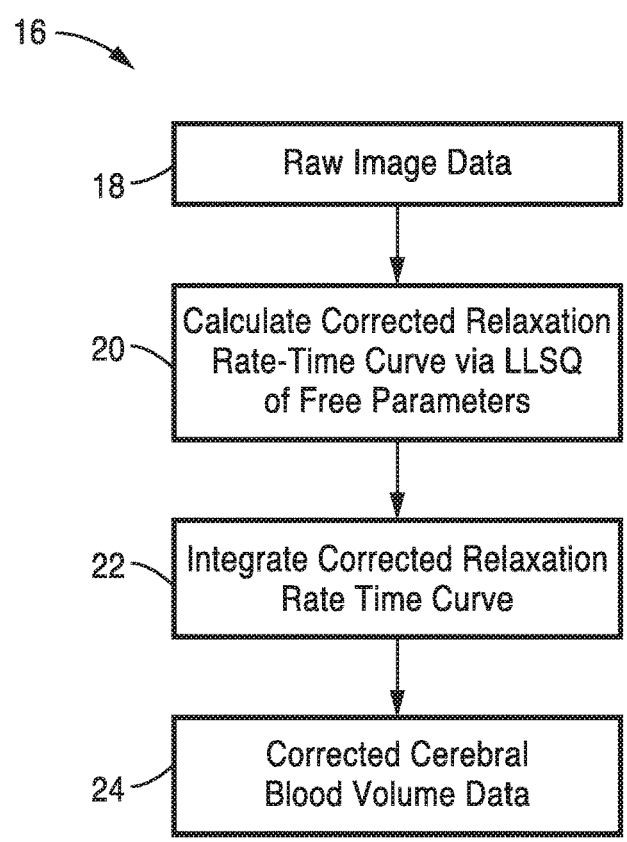
FIG. 2 shows a detailed flow diagram of the bidirectional leakage correction algorithm 16 of FIG. 1.

FIG. 2 shows a detailed flow diagram of the bidirectional leakage correction algorithm 16 of FIG. 1. The algorithm 16 comprises a transformation for post-processing leakage correction of the raw image data 14 (i.e. baseline signal comprising the uncorrected T2*-weighted MR images), and accounts for bidirectional contrast agent exchange between intra- and extravascular spaces.

At step 20, the corrected relaxation rate-time curve is calculated (via Eq. 7, which is based on the whole-brain average relaxation rate for non-enhancing voxels of Eq. 3 and Eq. 4). Linear least squares optimization (LLSQ) was used to determine the free parameters for in solving for Eq. 7.

At step 22, the corrected rCBV was computed from the integral of the corrected relaxation rate-time curve (Eq. 8) to output the corrected cerebral blood volume data at step 24, which may be in the form of transformed rCBV images.

While the bidirectional leakage correction algorithm 16 is shown in FIG. 2 outputting blood volume data, it is appreciated that the methods algorithm 16 may be modified to also generate dynamic contrast enhanced (DCE)—MRI parameters (e.g. $K_{trans}$, $k_{ep}$, $v_e$, etc.) using a single MRI acquisition, without need for additional/subsequent injections and/or perfusion scans. Thus, method 10 may be implemented to simultaneously obtain physiological characteristics pertaining to DSC-MRI (e.g. blood volume (e.g. rCBV) blood flow (e.g. rCBF), etc.) with physiological characteristics pertaining to DCE-MRI (e.g. vascular permeability parameters such as $K_{trans}$, $k_{ep}$, $v_e$, etc.), as these parameters reflect how the blood barrier has been compromised in certain conditions).

For example, bidirectional leakage correction algorithm 16 may include instructions for calculating $k_{trans}$ perfusion data according to Eq. 9:

$$K^{trans} = K_2 \frac{TE}{TR \cdot r_1 \cdot \int \Delta R_2^*(t') dt'} \left( \frac{e^{-\frac{TR}{T_{10}}}}{1 - e^{-\frac{TR}{T_{10}}}} - \frac{e^{-\frac{TR}{T_{10}}} \cdot \cos \alpha}{1 - e^{-\frac{TR}{T_{10}}} \cdot \cos \alpha} \right)^{-1} \quad \text{Eq. 9}$$

Figure 3:
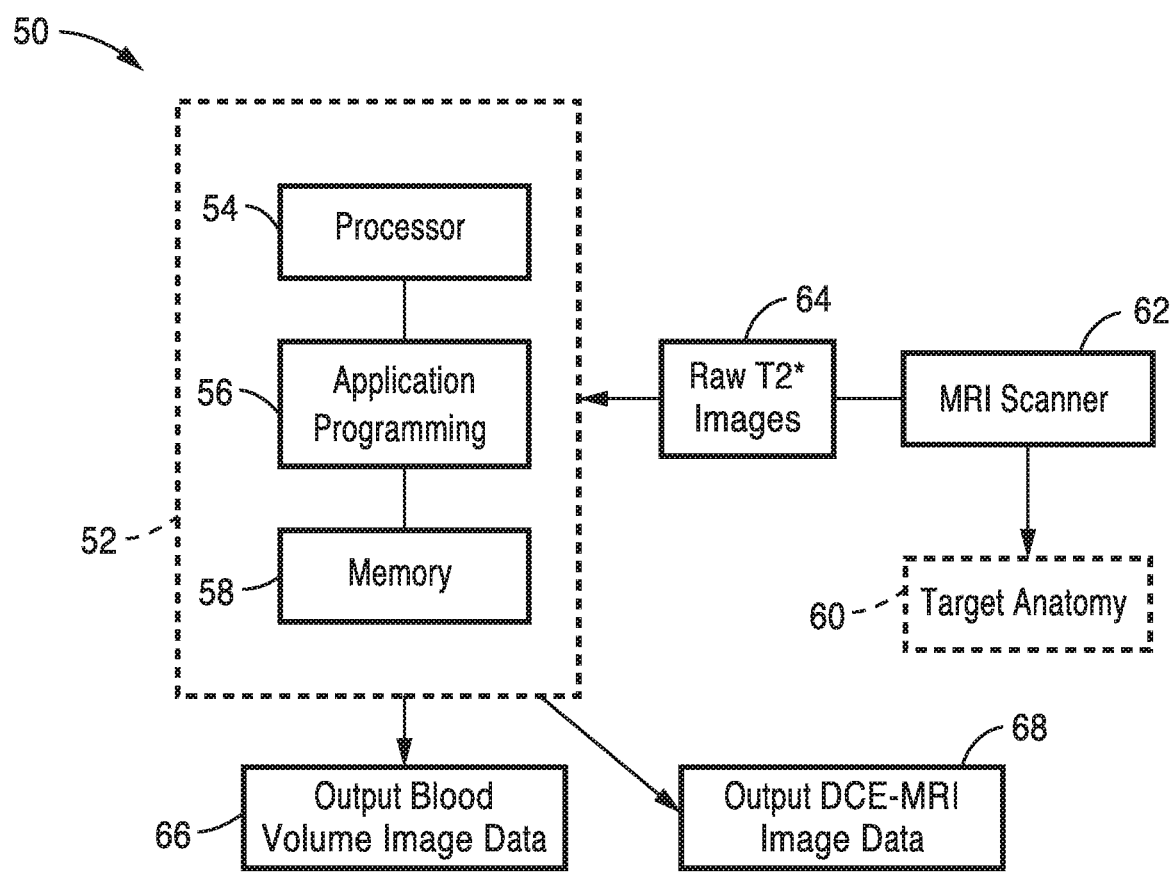
FIG. 3 shows a schematic diagram of a system 50 for leakage correction during magnetic resonance imaging in accordance with the present description.

FIG. 3 shows a schematic diagram of a system 50 for leakage correction during magnetic resonance imaging in accordance with the present description. System 50 includes a computer or server 52 comprising a processor 54, and application programming 56 stored in memory 58, the application programming 56 comprising instructions for receiving the raw data 64 (i.e. baseline signal comprising the uncorrected T2*-weighted MR images) of the target anatomy 60 from MRI scanner 62, and applying corrected leakage method 10 to output blood volume image data 66 and/or DCE-MRI image data 68. Application programming 56 may further include instructions for performing the bidirectional leakage correction algorithm 16, any of processing steps 20 and 22, or physiological characteristics pertaining to DCE-MRI, simultaneously without need for additional/subsequent injections and/or perfusion scans.

Application programming 56 may further include instructions for other indicators of evaluation of brain tumor vascularity and angiogenesis, including grading of newly diagnosed gliomas, guiding surgical interventions, evaluating response to therapy, and differentiating true tumor progression from treatment-related pseudo progression, etc.

Table 1 provides an example of instructions for performing rCBV correction via application programming 56 on computer processor 54.

1. Example 1

1.1 DSC-MRI and DCE-MRI Test Setup

DSC-MRI and DCE-MRI (Group 1) were retrospectively reviewed on images (acquired with 3T scanner, Siemens Trio or Skyra, Siemens Healthcare, Erlangen, Germany). Tests were performed at initial tumor progression (>2 sequential months of increasing contrast enhancement and worsening mass effect) in 21 patients (15 men; mean age 54 years, range 30-73) with histologically proven GBM treated with maximal surgical resection followed by radiotherapy and concurrent temozolomide. $T_1$ maps were generated from 5 pre-contrast $T_1$-weighted images (flip angle=5°, 10°, 15°, 20°, 30°) prior to DCE-MRI (16 slices, 130 time points, 5 s time resolution, TE/TR=1.87/5 ms, 25° flip angle, 3 mm slice thickness, 256×192 matrix, 24 cm FOV). The DCE-MRI was acquired for ~10 minutes, which is the waiting time between preload and DSC contrast injections for this study. Contrast agent bolus (0.1 mmol/kg) (Magnevist, Bayer HealthCare) was injected after 10-13 baseline images, serving as pre-load for DSC-MRI (gradient echo EPI, TE/TR=32/1840 ms, 35° flip angle, 120 time points, bolus injection after 20-25 baseline images, 9-20 slices, 5 mm slice thickness, 128×128 matrix size, 24 cm FOV). Conventional post-contrast T1-weighted imaging was subsequently performed. Patients were excluded if DCE-MRI or DSC-MRI was corrupted by motion or technical error.

All conventional and DCE-MRI images for each subject were registered to baseline DSC-MRI images using 12-degree of freedom affine transformation with a mutual information cost function. If needed, manual alignment was subsequently performed. To segment the contrast-enhancing tumor, custom scripts were employed and manually defined regions of lesion enhancement were manually defined, excluding hemorrhage and macro vessels. Regions were further constrained using empirical thresholds, excluding central necrosis, and segmentations were edited to exclude non-lesion voxels. ROIs were also selected in normal-appearing white matter for rCBV normalization.

All simulations and calculations were performed in MATLAB using custom scripts. Uncorrected rCBV was calculated from trapezoidal integration of the original DSC-MRI relaxation rate-time curve, $\Delta\hat{R}_2(t)$. The whole-brain average relaxation rate for non-enhancing voxels (Eq. 3-Eq. 4) was used for both the Unidirectional-model and the bidirectional exchange model of the present description. Linear least squares optimization was used to determine the free parameters for both the Bidirectional-model (via Eq. 7) and the Unidirectional-model (Eq. 5, with $k_{ep}=0$) algorithms, and corrected rCBV was computed from Eq. 8. The average runtime per patient in MATLAB was 19.5±6.7 s for the Bidirectional-model and 18.3±6.2 s for the Unidirectional-model (3.2 GHz Intel Core i5, 32 GB RAM). Tumor rCBV for each method was subsequently normalized to median rCBV within the normal appearing white matter ROI.

For each enhancing tumor voxel for all Group 1 patients, the Akaike Information Criterion (AIC) was computed between leakage-contaminated relaxation rate $\Delta\hat{R}_2(t)$ (Eq. 1) and its model fit (Eq. 5) for the Unidirectional-model and Bidirectional-model:

$$AIC = n \cdot \ln(RSS/n) + 2(p+1), \quad \text{Eq. 10}$$

where n is the number of fitted time points (injection to end of DSC-MRI acquisition), RSS is the sum of the squared residuals, and p is the number of free parameters (2 for the Unidirectional-model, 3 for the Bidirectional-model). Differences in the Unidirectional-model and Bidirectional-model AIC were calculated for all voxels where $k_{ep}>0$. Euclidean distance (square root of the sum of the squared differences) was also computed for the interstitial leakage relaxation rate curves, $\Delta\hat{R}_2(t)$, generated by the Unidirectional-model and Bidirectional-model corrections and DCE-MRI signal, where the DCE-MRI signal was upsampled from a 5-second resolution to a 1.8-second resolution to match that of the DSC-MRI data. Because interstitial leakage relaxation rate curves and DCE-MRI signal have units of 1/sec and mM, respectively, both were standardized to an area under the curve equal to unity and vectorized for computation of Euclidean distance. Higher AIC and ED imply worse fits. Pre-treatment scans were acquired at a maximum of one month prior to bevacizumab therapy, while post-treatment scans were acquired at a maximum of two months subsequent to initiated therapy.

DSC-MRI imaging biomarkers, e.g. $k_{ep}$ and rCBV, were derived as described above. DCE-MRI imaging biomarkers, e.g. $k_{ep}$ and $K_{trans}$, were derived via a fit to the original Tofts model. As detailed above, the temporal resolution of the DCE-MRI data was up-sampled to match the DSC-MRI data. For the DCE-MRI analysis, the "whole brain average" served as the arterial input function for the DCE model fit. Voxels with highly fluctuating time courses in either the DSC or DCE images were eliminated from the analysis. Voxel-wise correlations between the DSC- and DCE-derived parameters were performed in MATLAB within contrast-enhancing tumor only.

1.2. Experimental Results

Figure 4A:
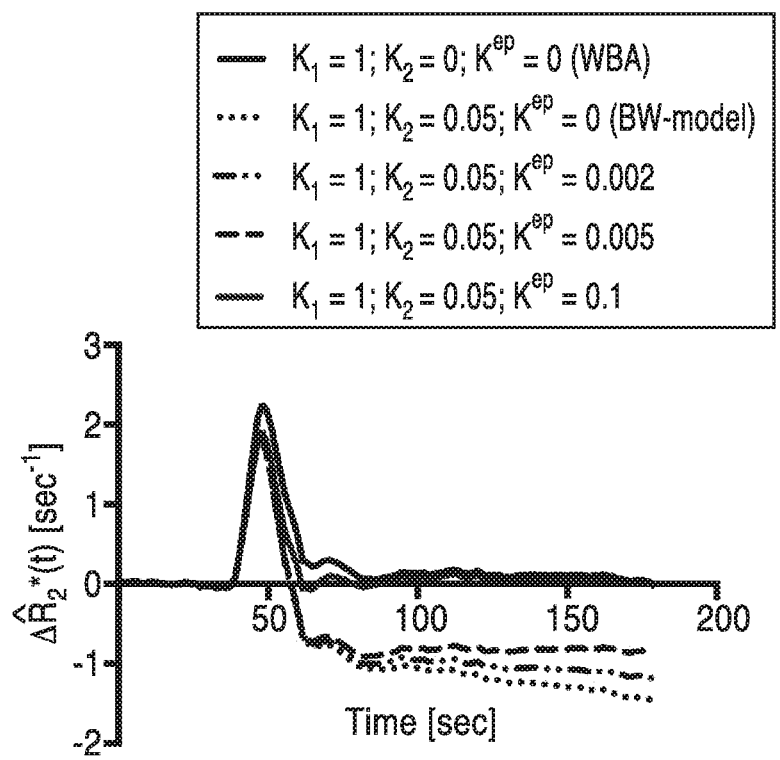
FIG. 4A shows a plot comparing simulated total leakage contaminated relaxation rate, $\Delta \hat{R}^*_2(t)$ for Unidirectional and Bidirectional models.
Figure 4B:
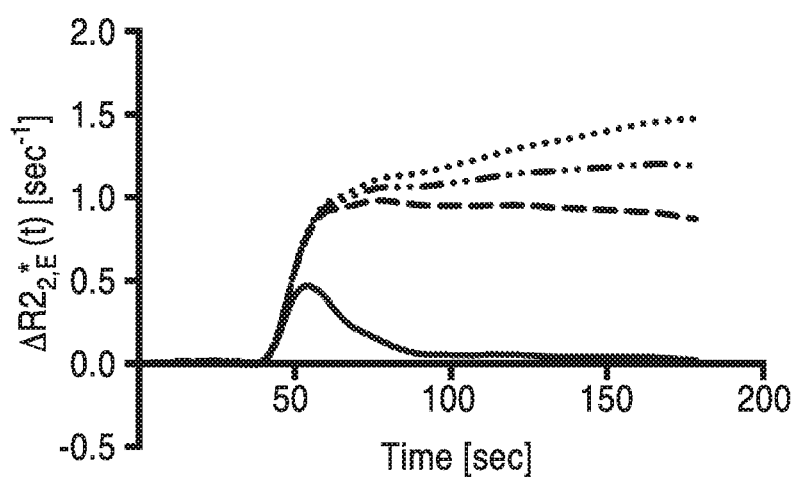
FIG. 4B shows a plot comparing a component from interstitial leakage for Unidirectional and Bidirectional models.

FIG. 4A shows a plot comparing simulated total leakage contaminated relaxation rate, $\Delta\hat{R}^*_2(t)$ for Unidirectional and Bidirectional models. FIG. 4B shows a plot comparing a component from interstitial leakage, $\Delta\hat{R}^*_2(t)$, for Unidirectional and Bidirectional models. Both FIG. 4A and FIG. 4B show plots for various conditions according to the Tofts model, assuming T1-dominant leakage-associated relaxation enhancement. The whole-brain average relaxation rate, $\Delta\bar{R}^*_2(t)$, was chosen from a sample patient in Group 1, and corresponds to the curve with $K_1=1$, $K_2=0$, and $k_{ep}=0$. To simulate the Unidirectional-model, we set $K_2=0.05$ (adding T1-dominant leakage), with $k_{ep}=0$, and $\Delta\hat{R}^*_2(t)$ rises over time in the absence of washout ($k_{ep}=0$). For nonzero $k_{ep}$ (0.002 or 0.005), interstitial washout is added to the Bidirectional-model of $\Delta\hat{R}^*_2(t)$, with less rise in $\Delta R^*_2(t)$ and closer approximation of the tail of $\Delta\hat{R}^*_2(t)$ to $\Delta\bar{R}^*_2(t)$, reflecting tumors with different contrast agent pharmacokinetics. For $k_{ep}=0.1$, the tail of $\Delta R^*_2(t)$ approaches zero, but because the first-pass of $\Delta\hat{R}_2(t)$ differs from that of $\Delta\bar{R}^*_2(t)$, correction of relaxation rate curves at "artery-like" voxels using $K_1$ and $K_2$ is still required to achieve accurate rCBV estimates.

Figure 4C:
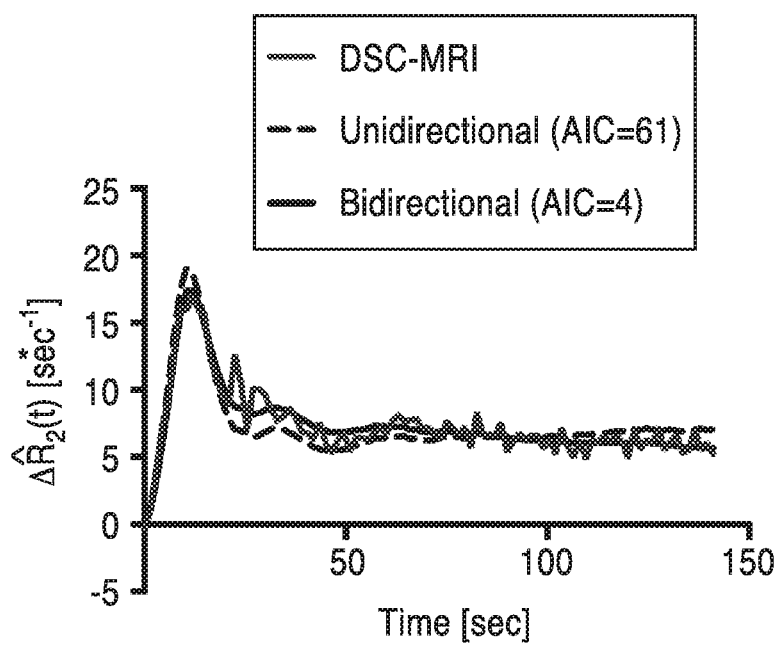
FIG. 4C shows a plot of sample $\Delta \hat{R}^*_2(t)$ over time with superimposed Unidirectional-model and Bidirectional-model fit relaxation rate curves in relation to DSC-MRI.

FIG. 4C shows a plot of sample $\Delta\hat{R}^*_2(t)$, with T2*-dominant leakage-associated relaxation enhancement, for a Group 1 patient, with superimposed Unidirectional-model and Bidirectional-model fit relaxation rate curves in relation to DSC-MRI. In this example, the Unidirectional-model overestimates the first-pass curve, underestimates the second and third passes, and overestimates the tail. The Bidirectional-model better approximates $\Delta\hat{R}_2(t)$ over all time points, visually, and has substantially improved AIC, quantitating an improved fit to the total leakage contaminated relaxation rate curve.

Figure 4D:
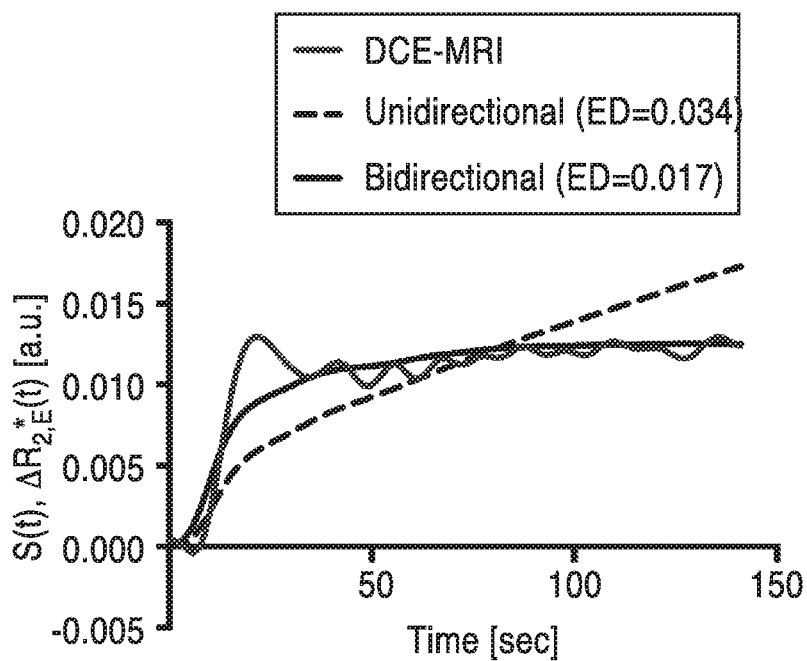
FIG. 4D show a plot of standardized DCE-MRI signal for the tumor voxel used in FIG. 4C, with superimposed standardized interstitial leakage relaxation rate curves, $\Delta \hat{R}^*_2(t)$, from the Unidirectional-model and Bidirectional-model.

FIG. 4D show a plot of standardized DCE-MRI signal for the tumor voxel used in FIG. 4C, with superimposed standardized interstitial leakage relaxation rate curves, $\Delta R^*_2(t)$, from the Unidirectional-model and Bidirectional-model. The standardized interstitial leakage relaxation rate continually rises over time for the Unidirectional-model, whereas it better tracks standardized DCE-MRI for Bidirectional-model with substantially improved Euclidean distance.

Figure 5:
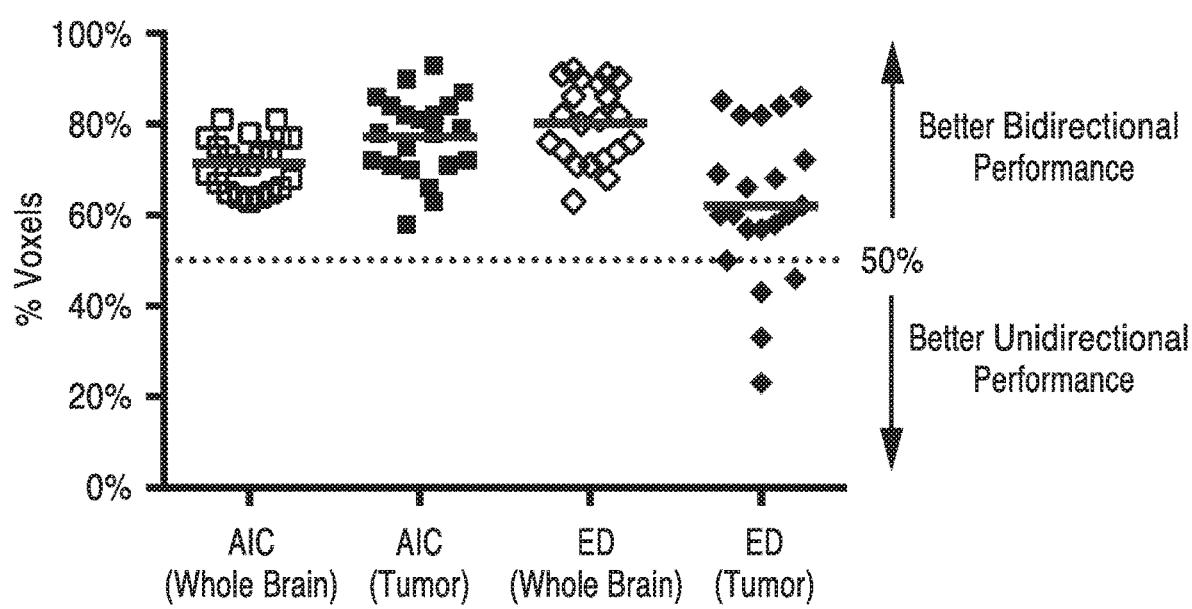
FIG. 5 shows a plot comparing Bidirectional-model performance against the Unidirectional-model for AIC and Euclidean distance metrics in whole brain and tumor.

FIG. 5 shows a plot of the percentage of voxels where the Bidirectional-model outperformed Unidirectional-model for AIC and Euclidean distance metrics in whole brain and tumor for the 21 GBM patients in Group 1. The Bidirectional-model had better AIC performance than Unidirectional-model in greater than 50% of whole-brain (mean±standard deviation=71%±6%, p<0.0001) and tumor (77%±9%, p<0.0001) voxels in all patients, and better Euclidean distance performance in greater than 50% of whole-brain voxels (80%±9%, p<0.0001) for all patients, and tumor voxels (62%±17%, p=0.0041) for 17 of the 21 patients. All were statistically significant for a one-sample t-test with null hypothesis of 50%.

A voxel-wise correlation was performed between the DSC-derived imaging biomarkers from the bidirectional leakage correction algorithm ($k_{ep}$ and rCBV) with the DCE-derived imaging biomarkers ($k_{ep}$ and $K_{trans}$). Across the 21 patients, the correlations between the two $k_{ep}$ measurements was 0.74±0.13 across the 21 patients, with a weak correlation between the Pearson's correlation coefficient and tumor size (r=0.11). FIG. 6A through FIG. 6C show images demonstrating the correlation between DSC- and DCE-derived $k_{ep}$. FIG. 6A shows a post-contrast, T1-weighted image, whereas FIG. 6B and FIG. 6C show images of DSC-derived $k_{ep}$ and DCE-derived $k_{ep}$, respectively. FIG. 7 shows a plot of a correlation test performed between the bidirectional model-derived rCBV and DCE-derived $K_{trans}$, with a moderate correlation of 0.49±0.22. Finally, the correlation between the same rCBV and $k_{ep}$ was r=0.29±0.26.

Figure 8A:
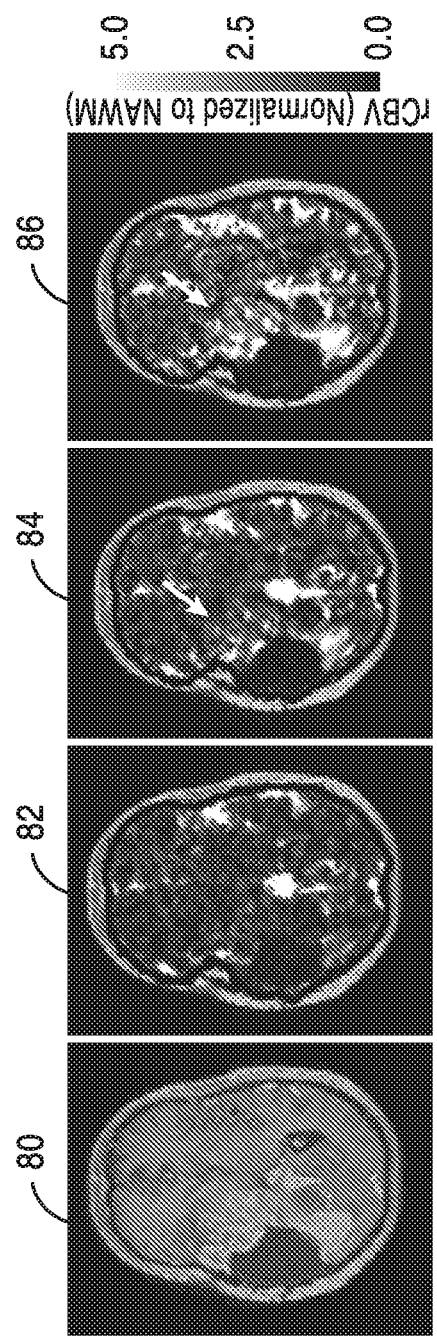
FIG. 8A shows a series of images comparing rCBV maps processed from T1-weighted images without leakage correction against rCBV maps with Unidirectional-model correction and rCBV maps with Bidirectional-model correction, in two different GBM patients with T1-dominant leakage (K2>0) on average in contrast enhancing tumor voxels.
Figure 8B:
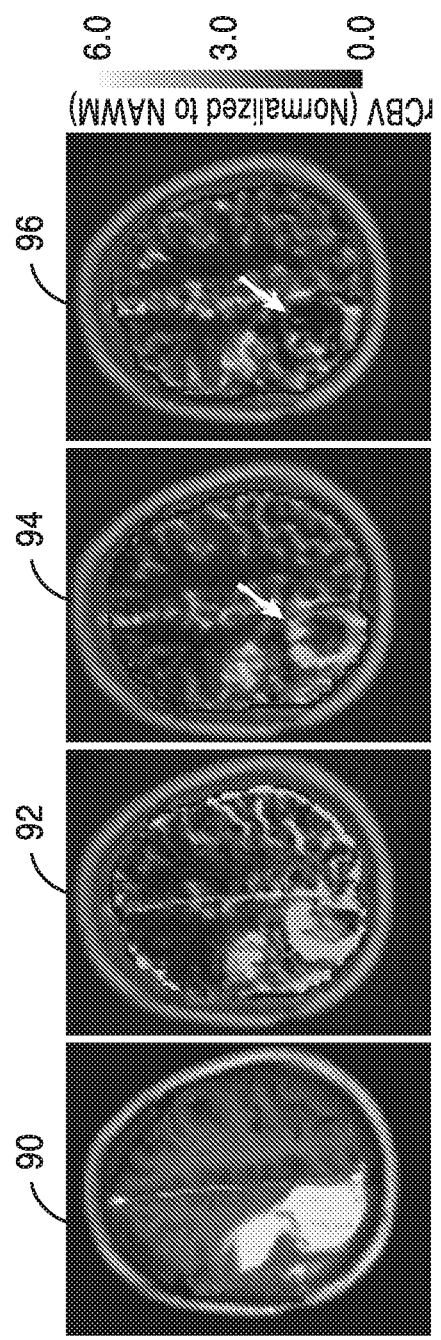
FIG. 8B show a series of images comparing rCBV maps processed from T1-weighted images without leakage correction against rCBV maps with Unidirectional-model correction and rCBV maps with Bidirectional-model correction, in two different GBM patients with T2*-dominant leakage (K2<0).

FIG. 8A and FIG. 8B show a series of images comparing rCBV maps 82, 92 processed from T1-weighted images 80, 90) without leakage correction against rCBV maps 84, 94 with Unidirectional-model correction and rCBV maps 86, 96 with Bidirectional-model correction, in two different GBM patients from Group 1: one with T1-dominant leakage (K2>0) on average in contrast enhancing tumor voxels (FIG. 8A), and the other (FIG. 8B) with T2*-dominant leakage (K2<0). For all Group 1 patients, average uncorrected rCBV was 1.98±1.24, average Unidirectional-model corrected rCBV was 1.59±0.89, and average Bidirectional-model corrected rCBV was 1.35±0.80. The average difference between Unidirectional-model corrected and Bidirectional-model corrected rCBV was 16.6±14.0%. A closer inspection of the T2*-dominant versus T1-dominant voxels (as defined by a negative or positive $K_2$, respectively) revealed that the difference between the two correction methods in T2*-dominant voxels was 37.7±42.6%, while the same metric for T1-dominant voxels was 5.8±3.4%.

2. Example 2

2.1 Test Setup

The goal of this study was to systematically evaluate the effects of various leakage correction strategies on the fidelity of rCBV estimation utilizing simulated DSC-MRI data. Specifically, the following parameters were evaluated: flip angle; echo time (TE); repetition time (TR); preload dosage and incubation time; truncation of the relaxation rate-time curve, $\Delta R2*(t)$; and post-processing leakage correction technique, including a new bidirectional leakage correction algorithm shown to improve rCBV estimation in brain tumors.

Simulated DSC-MRI signal curves for brain tumors were generated via: 1) selection of pulse sequence parameters; 2) construction of the leakage-affected intravascular and extravascular, extracellular space (EES) contrast agent concentration-time series based upon tumor characteristics (Eq. 7); and 3) estimation of rCBV using no leakage correction, unidirectional leakage correction, or bidirectional leakage correction accounting for bidirectional contrast agent flux between the vasculature and EES.

All combinations of the following DSC-MRI parameters were tested: Flip angle=35°, 60°, and 90°; TE=15, 25, 35, 45, and 55 ms; TR=1.0, 1.5, and 2.0 s; fractional preload+bolus dosage=¼+¾ (6 mM total, single dose), ½+½ (6 mM total, single dose), and 1+1 (12 mM total, double dose).

A generic AIF was generated using the following approximation:

$$C_\infty(t) = A(t/t_p^2)e^{-\frac{t}{t_p}} + B(-e^{-t/t_p})$$ Eq. 11 where A=200 mM·s, B=1.75 mM, and $t_p$=2 s and the peak concentration was 6.0 mM for the full dose and scaled appropriately for the preload dosages and post-preload bolus injections. For preload simulations, the composite AIF was constructed as the superposition of the preload injection AIF and the bolus AIF delayed by the specified incubation time.

The blood plasma contrast agent concentration was computed by convolving the AIF with an exponential residue function:

$$C_p(t) = \frac{\rho}{k_H} \cdot CBF \cdot \int_0^t C_\infty(t) \cdot e^{-\frac{(t-\tau)}{MTT}} d\tau,$$ Eq. 12 where ρ is the density of brain tissue (1.04 g/m L), $k_H$ is the hematocrit difference between capillaries and large vessels (0.73), and MTT is the mean transit time.

The EES contrast agent concentration was computed as follows:

$$C_E = K^{trans} \cdot \int_0^t C_\infty(t) \cdot e^{-\left(\frac{K^{trans}}{v_e}\right)(t-\tau)} d\tau.$$ Eq. 13

The relaxivity-time curves were obtained from EQ. 7. For each relaxivity-time curve, S(0) was computed as the median of the first 30 s "baseline" signal.

Specific tumor characteristics were estimated based on previous data, including CBV=5 mL/100 g, CBF=60 mL/100 g/min, and $T_{20}*$=0.05 s. The blood volume fraction, vp, was set equal to ρ/kH·CBV. Relaxivity values for gadolinium were assumed to be $r_1$=3.6 mM$^{-1}$s$^{-1}$, $r_{2,P}*$=87 mM$^{-1}$s$^{-1}$, and $r_{2,E}*$=30 mM$^{-1}$s$^{-1}$. Monte Carlo simulations were performed using the following values: $K_{trans}$ 0.214±0.04 min$^{-1}$, $v_e$=0.722±0.17, $T_{10}$=1.59±0.40 s, $r_{2,P}*$=87.0±17.4 mM$^{-1}$s$^{-1}$, and $r_{2,E}*$=30±6 mM$^{-1}$s$^{-1}$. $K_{trans}$ and $v_e$ were chosen by using the average values and standard deviations from literature. $T_{10}$ was estimated from variable flip angle mapping from 25 glioblastomas (five pre-contrast $T_1$ flip angle maps were acquired for each patient (e.g. at 2°, 5°, 10°, 15°, 30°) and fitted using a Levenberg-Marquardt non-linear approach to the gradient-echo signal equation. The variance for $r_{2,P}*$ and $r_{2,E}*$ are understood to be not well-defined in the literature and were chosen to be 20% to approximately match the standard deviations of the other parameters.

$K_P$, the susceptibility calibration factor, was chosen to generate a 40% peak signal drop in gray matter, for which CBF=60 mL/100 g/min and CBV=4 mL/100 g were chosen. The whole brain average was selected as the average of 1,000 white matter voxels (including noise), with CBF=25 mL/100 g/m in and CBV=2 mL/100 g.

The relative contrast-to-noise ratio (CNR) was estimated as C·sin(α), where α is the flip angle and C is the relative contrast agent dose (½, ¾, or 1 dose). Absolute CNR was estimated by scaling the relative CNR by average SNR (SNR=40.5) from a sample of 25 human glioblastomas (flip angle of 35°, TE=32 ms, and TR=1.8s), based on the pre-contrast baseline, then extrapolating to the other acquisition conditions. CNR for different TE and TR were estimated using the same procedure and scaling by $$e^{-\frac{TE}{T2} \cdot (t-\tau)} \left(1 - e^{-\frac{TR}{T_1}}\right),$$

relative to the aforementioned single-echo protocol, where T10 and T20 are the underlying tissue characteristics prior to the DSC bolus injection. Noise was added to the final DSC-MRI signal-time curve via random generation of a number from the normal distribution with zero mean and a standard deviation equal to the peak signal intensity divided by CNR.

Uncorrected rCBV was computed by integrating $\Delta R2^*(t)$, while leakage-corrected rCBV was obtained using either Unidirectional or Bidirectional leakage correction algorithms. The "ground truth" ($\Delta R2^*(t)_{gt}$) estimate of rCBV was calculated under conditions of no noise with $K_{trans}=0$. Percentage error from ground truth was calculated for uncorrected and leakage corrected rCBV estimates with added noise.

To estimate the effects of preload incubation time, we compared estimates of rCBV with delays of 5-10 minutes between preload and bolus injection. To estimate the effects of truncating $\Delta R2^*(t)$ on rCBV estimates, we compared rCBV estimates using the first 0.5, 1.0, 1.5, or 2.0 minutes of the post-baseline $\Delta R2^*(t)$ as well as the entire 2.5 minute data.

For each set of pulse sequence parameters, Gaussian noise was added to each time point with normal distribution (zero mean, standard deviation equal to maximum signal scaled by CNR), and tumor characteristics were generated according to the normal distributions described above. A Monte Carlo simulation was conducted using 250 randomly chosen tumors, with random noise, for each set of pulse sequence parameters. Percentage error was calculated using the computed rCBV and the "ground truth" rCBV. The 95% confidence intervals of percentage error were subsequently generated for the uncorrected rCBV and each of the leakage correction algorithms and are shown in each of the figures. A protocol comprising a 60° flip angle, TE=35 ms, TR=1.0s, ¼ preload dose+¾ DSC-MRI, and waiting time=5 min was chosen as the template.

2.2 Experimental Results

Figure 9A:
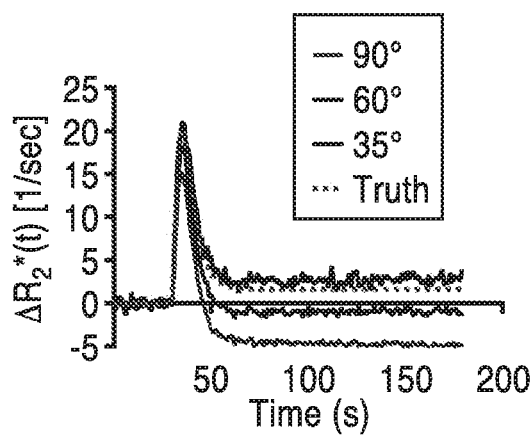
FIG. 9A shows a plot of $\Delta R2^*(t)$ generated using different flip angles with noise along with $\Delta R2^*(t)gt$.
Figure 9B:
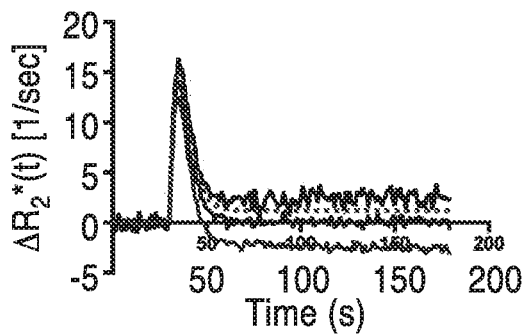
FIG. 9B shows a plot of $\Delta R2^*(t)$ using dose of preload and dose for DSC-MRI bolus, which increases T2*-weighting for all flip angles.
Figure 9C:
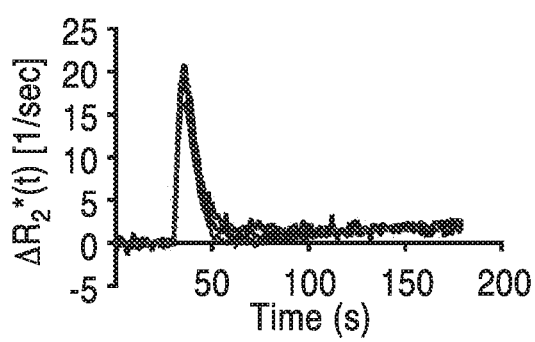
FIG. 9C shows a plot of corrected $\Delta R2^*(t)$ using unidirectional leakage correction without preload.
Figure 9D:
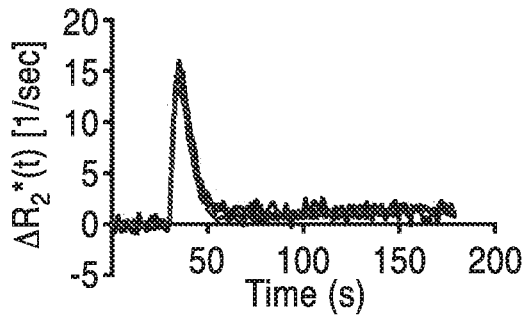
FIG. 9D shows a plot of corrected $\Delta R2^*(t)$ using unidirectional leakage correction after preload.
Figure 9E:
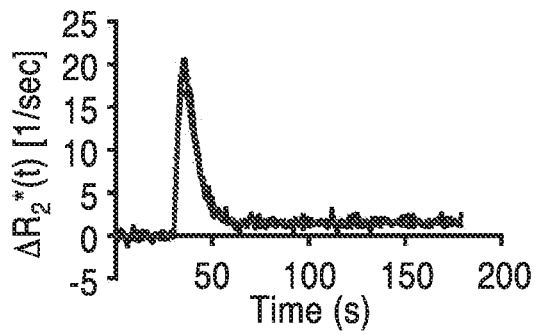
FIG. 9E shows a plot of corrected $\Delta R2^*(t)$ using bidirectional leakage correction without preload.
Figure 9F:
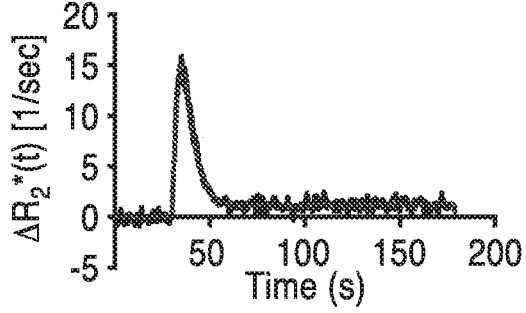
FIG. 9F shows a plot of Corrected $\Delta R2^*(t)$ using bidirectional leakage correction after preload.

FIG. 9A through 9F summarize the effects of flip angle on $\Delta R2^*(t)$ for a particular combination of TE, TR and preload dosage (35 ms, 1.0s, ¼ preload+¾ DSC-MRI, respectively). Without preload (FIG. 9A), there is reduced $T_1$-weighting and increased $T_2^*$-weighting with smaller flip angles as manifested by higher $\Delta R2^*(t)$, best seen in the "tail". Preload administration increases $T_2^*$-weighting (FIG. 9B). In this case, without preload, the 35° relaxivity-time curve is closest to "ground truth" ($\Delta R2^*(t)_{gt}$), while the 60° and 35° curves are equally close to the truth curve after preload (¼ dose+¾ dose DSC-MRI). Based on the formula used for CNR, the 35° flip angle also yields the most noise, as exemplified in the preload DSC-MRI curve. FIG. 9C-9F show "corrected" $\Delta R2^*(t)$ using the Unidirectional and Bidirectional correction algorithms. For both non-preload and preload administration, Unidirectional-corrected $\Delta R2^*(t)$ varied greater from $\Delta R2^*(t)_{gt}$ across all tested flip angles as compared to Bidirectional-corrected $\Delta R2^*(t)$, particularly right after the first pass of the bolus.

Figure 10A:
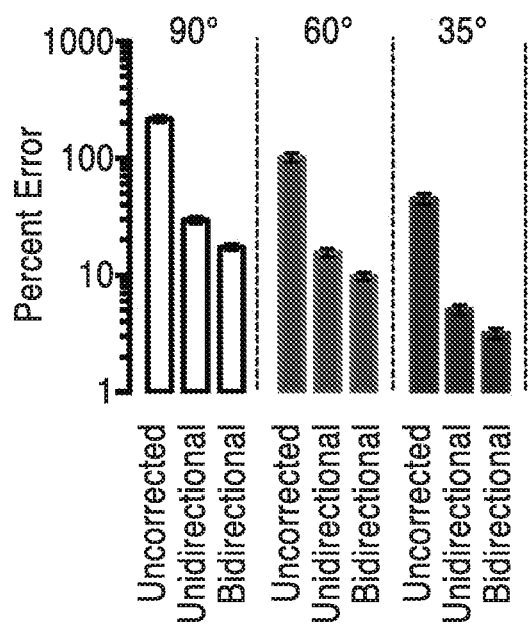
FIG. 10A shows a graph of percentage error (with 95% CI) of the estimated rCBV for different flip angles and leakage correction strategies, without use of preload, compared to "ground truth" rCBV.
Figure 10B:
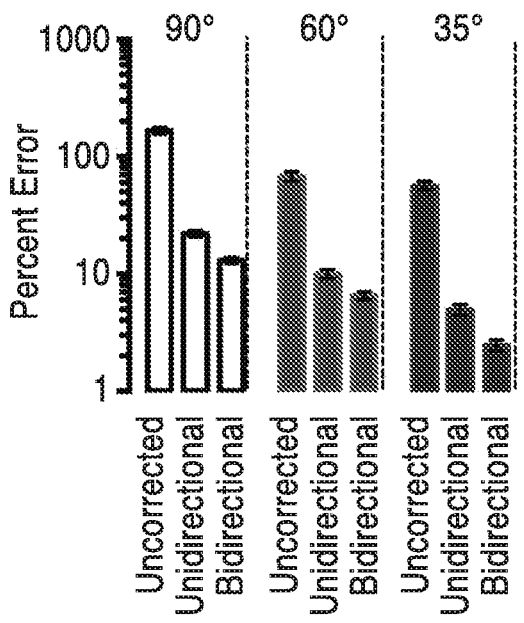
FIG. 10B shows a graph of percentage error (with 95% CI) of the estimated rCBV for different flip angles and leakage correction strategies, with use of. dose preload, compared to "ground truth" rCBV.
Figure 11A:
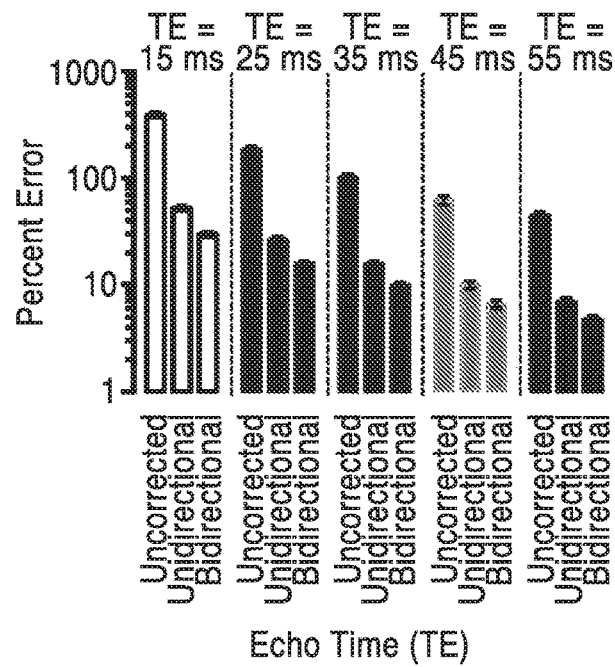
FIG. 11A and FIG. 11B show graphs of percentage error in rCBV estimation for different TEs and leakage correction strategies for no preload (FIG. 11A) and ¼ dose preload followed by ¾ dose DSC bolus injection (FIG. 11B).
Figure 11B:
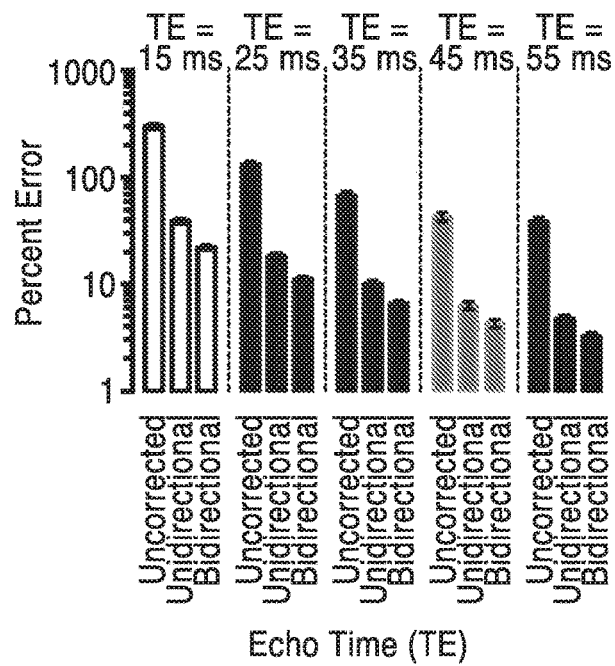
Figure 12A:
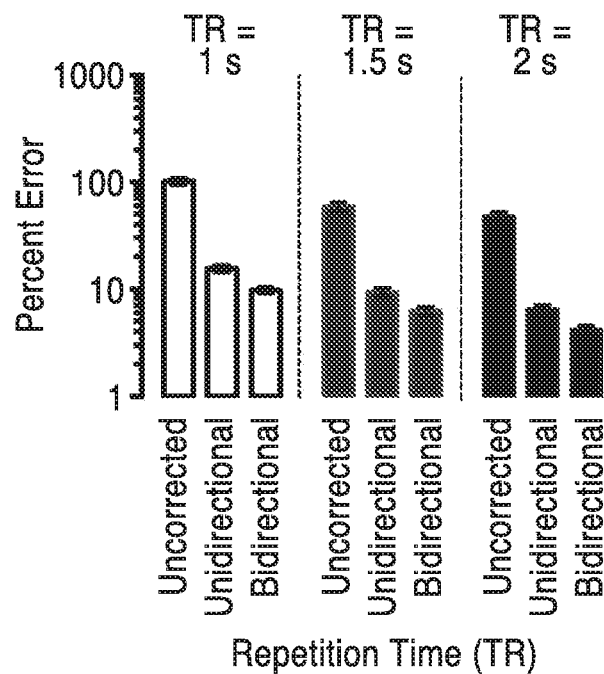
FIG. 12A and FIG. 12B show graphs of percentage error in rCBV estimation for different TRs and leakage correction strategies for no preload (FIG. 12A) and ¼ dose preload followed by ¾ dose DSC bolus injection (FIG. 12B).
Figure 12B:
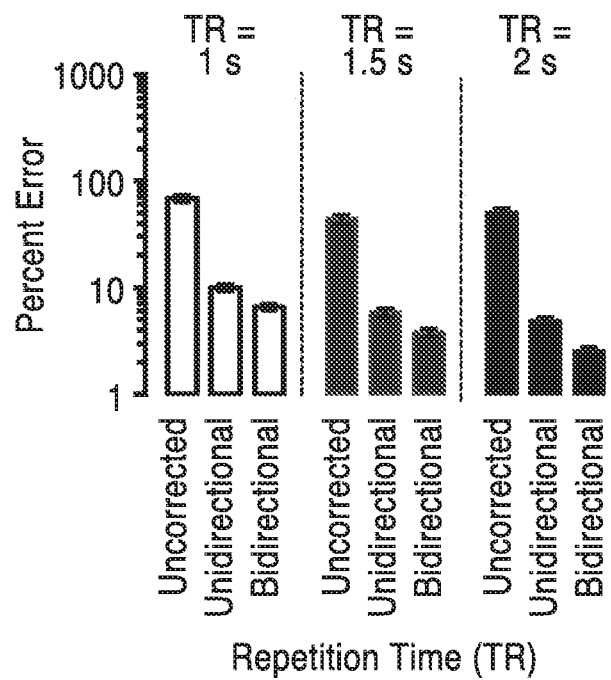

FIG. 10A and FIG. 10B show graphs illustrating the percentage errors for uncorrected, Unidirectional, and Bidirectional rCBV estimates, as compared to $\Delta R2^*(t)_{gt}$, for different flip angles for no preload (FIG. 10A) and ¼ preload+¾ DSC-MRI (FIG. 10B). With this particular combination of TR/TE/preload dosage, the 35° flip angle has the lowest error. Furthermore, error after both Unidirectional and Bidirectional leakage corrections tracked with error in the uncorrected rCBV, i.e., the lower error in uncorrected rCBV corresponded with lower error after leakage correction. For all tested flip angles, uncorrected rCBV estimates have the highest error, followed by the Unidirectional and then the Bidirectional estimates.

FIG. 11A through FIG. 12B demonstrate the impact of TE and TR on rCBV fidelity for a particular flip angle and preload dosage. It was found that longer TEs increase the $T2^*$-weighting of $\Delta R2^*(t)$ (60° flip angle, TR=1.0s).

Without preload (FIG. 11A), TE=55 ms yielded the most accurate $\Delta R2^*(t)$ for all three correction strategies using all leakage correction strategies.

With ¼ dose preload (FIG. 11B), TE=45 ms-55 ms performed more similarly, though the 55 ms performed slightly better.

Post-hoc leakage correction error tracked with uncorrected error in these examples. It was further shown that increased $T2^*$-weighting (or decreased T1-weighting) occurs with longer TR. Independent of preload, TR≥1.5 s yielded $\Delta R2^*(t)$ with less error compared with $\Delta R2^*(t)_{gt}$ for 60° flip (FIG. 12A and FIG. 12B) for the chosen flip angle, TE, and preload dosage. In general, rCBV error using the three methods were linearly correlated.

Figure 13:
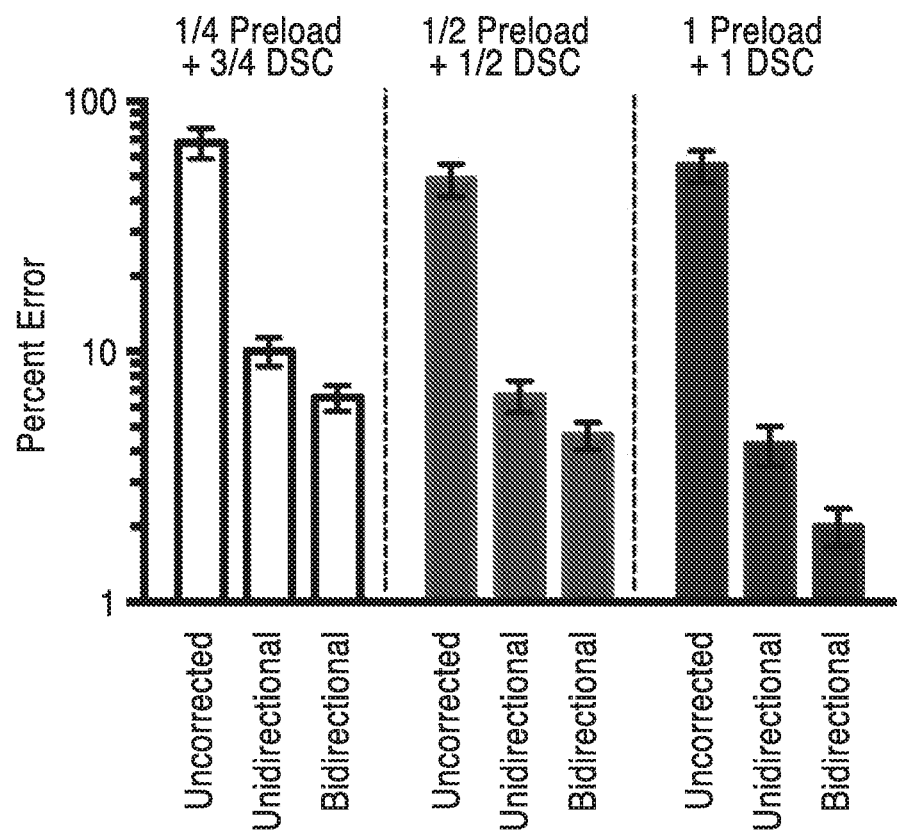
FIG. 13 shows a graph of the percent errors in rCBV for each preload dosage with 95% CI.

Preload primarily increases $T2^*$-weighting and reduces T1-weighting in $\Delta R2^*(t)$. For parameters of 60° flip angle, TE=35 ms, TR=1.5 s, 1 preload+1 bolus dosing yielded higher $\Delta R2^*(t)$ fidelity compared to "ground truth" $\Delta R2^*(t)$ than the ¼+¾ and ½+½ dosing schemes (FIG. 13). Even though the ½+½ and 1+1 dosing schemes had approximately the same uncorrected rCBV percent error, the post-hoc leakage correction algorithms benefited from the higher CNR that the full DSC-MRI dose provides.

With respect to dynamic EES contrast agent concentration with and without preload, the up-slopes of the concentration curves were found to be almost identical, indicating that preload appears to act not by decreasing the concentration-dependent rate of contrast agent efflux, but rather by decreasing baseline tissue T1 prior to bolus injection, as well as increasing $T2^*$-weighting.

Figure 14A:
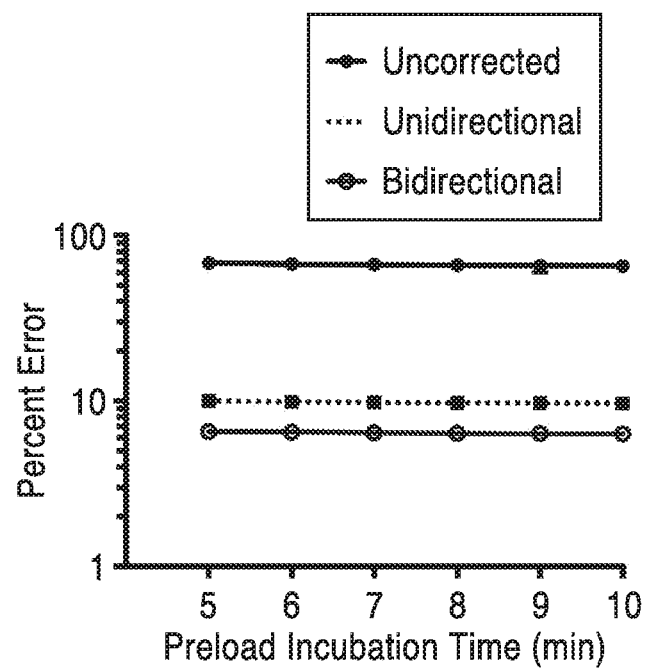
FIG. 14A is a plot illustrating the effects of preload incubation time on rCBV estimation when using preload.
Figure 14B:
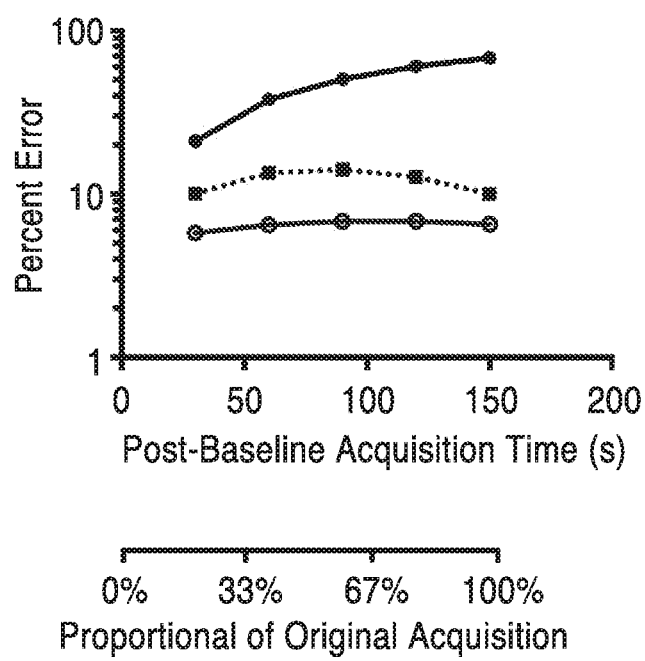
FIG. 14B is a plot illustrating the effects of truncation of the $\Delta R2^*(t)$ curves and leakage correction strategies on rCBV estimation when using a ¼ dose preload followed by ¾ dose DSC bolus injection.

We then investigated the effects of preload incubation time and data truncation on rCBV fidelity. Using incubation times of 5-10 minutes, the change in rCBV error is virtually similar, with a slight, gradual decrease in error from 5 min to 10 min (FIG. 14A). Next, because rCBV is computed from the integration of $\Delta R2^*(t)$, one strategy for mitigating leakage effects is truncating $\Delta R2^*(t)$ after the first pass. As expected, the less data used for computing rCBV, the lower the percent error for uncorrected rCBV (FIG. 14B). For Unidirectional rCBV, mean percent error is lowest when the full data is used. Interestingly, for Bidirectional rCBV, percentage error was lowest at 30s.

Using the bidirectional leakage correction algorithm, which outperformed the unidirectional leakage correction algorithm across all acquisition scenarios by a factor of 1.9±0.4, we attempted to take a global view of all combinations of acquisition strategies (flip angle, TE, TR, and preload dosage) to identify the "best acquisition strategies" that yield the highest fidelity in rCBV estimation.

Overall, the "best" protocol with the lowest overall mean percentage error utilized a 60° flip angle, TE/TR=35/1000 ms with 1 dose preload, using the bidirectional correction; however, there were multiple protocols whose 95% C Is overlapped (Table 2), suggesting there are several strategies that could be used to get similar rCBV estimates. In general, the best performing strategies were those that balanced both T1- and T2*-weighting secondary to contrast agent extravasation, with mean uncorrected rCBV error<70% for all of the "optimal" strategies with 1 total dose of contrast and <80% for those with 2 total doses of contrast agent, as opposed to much larger error for other protocols. Preload did not necessarily depress percent error, as evidenced by the 35° flip angle, in which higher preload dosages could "overshoot" the "ground truth". The best acquisition strategies (flip angle/TE/TR and contrast dose allocation for preload and bolus) for each preload dosing were the following: 1) 35°/35 ms/1.5s with no preload and full dose for DSC-MRI, 2) 35°/25 ms/1.5s with ¼ dose preload and ¾ dose bolus, 3) 60°/35 ms/2.0s with ½ dose preload and ½ dose bolus, and 4) 60°/35 ms/1.0s with 1 dose preload and 1 dose bolus. The 90° flip angle only appeared as an optimal strategy with 1 dose preload and 1 dose bolus.

3. Example 3

3.1 Test Setup

A digital reference object (DRO), comprising 1,000 unique voxels, was created using a validated computational approach. Each voxel in the DRO contained vascular and cellular structures that determine the temporal CA $T_2^*$ relaxivity. The tissue structures span a realistic range of vascular and cellular volume fractions, (which define CBV, $V_e$, and Vi).

A database of 50 DSC-MRI patients was used to train the DRO to yield signals that recapitulate clinical data including: magnitude of T1 and T2* effects, PSR, CBF, CBV, PS distribution, and CBF and CBV correlation.

The DRO was also validated against a dual-echo DSC-MRI database in order to verify the correct magnitude of T1 and T2* effects.

Signals (@3T) were computed using a range of acquisition parameters: TR (1-2 sec), TE=30, Flip Angle (60° and 90°). Multiple pre-load dosing schemes were considered (presented as a fraction of a total dose): [0,1], [¼, ¾], [½, ½], [½, 1], and [1,1]. Leakage correction was performed according to the Unidirectional (UD) model, and the Bidirectional (BD) model incorporated in the systems and methods of the present description.

3.2 Experimental Results

Figure 15A:
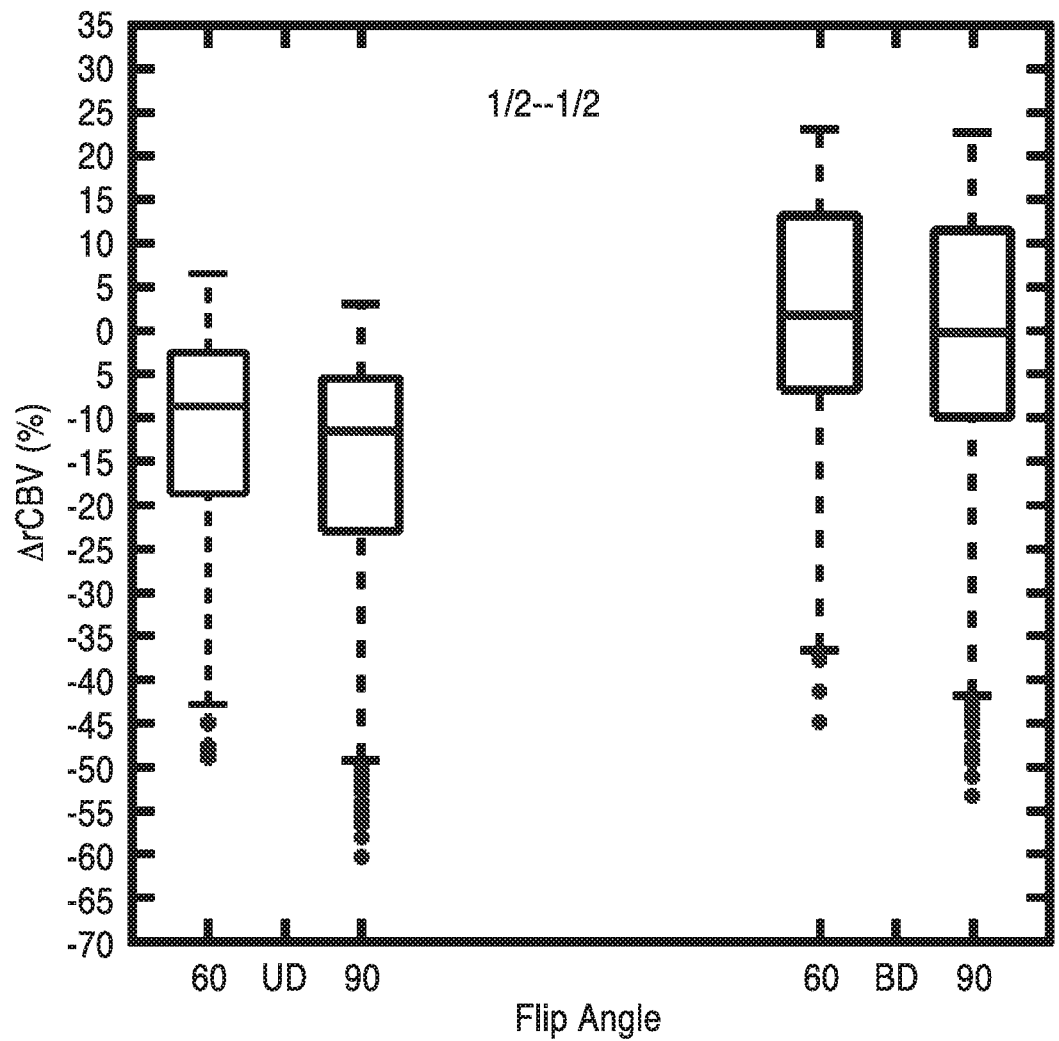
FIG. 15A shows a plot comparing results for Unidirectional (UD) leakage detection and Bidirectional (BD) leakage detection at a flip Angle of 60° and 90° for a pre-load dosing scheme of ½-½.
Figure 15B:
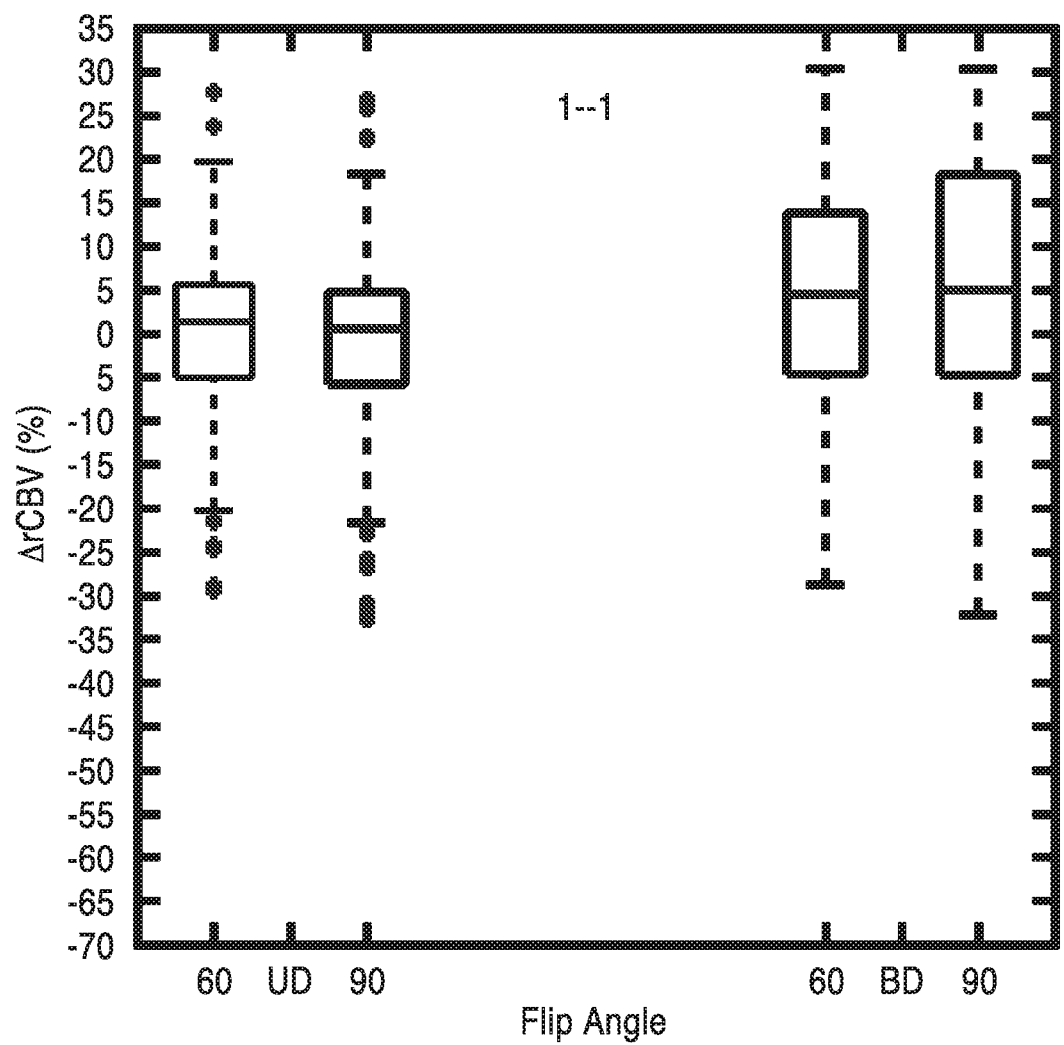
FIG. 15B shows a plot comparing results for Unidirectional (UD) leakage detection and Bidirectional (BD) leakage detection at a flip Angle of 60° and 90° for a pre-load dosing scheme of 1-1.

FIG. 15A shows a plot comparing results for Unidirectional (UD) leakage detection and Bidirectional (BD) leakage detection at a flip Angle of 60° and 90° for a pre-load dosing scheme of ½-½. FIG. 15B shows a plot comparing results for Unidirectional (UD) leakage detection and Bidirectional (BD) leakage detection at a flip Angle of 60° and 90° for a pre-load dosing scheme of 1-1.

In general, CBV data that was acquired with no-preload underestimates the true value, even with leakage correction. For Unidirectional (UD) leakage correction, there appears to be no difference between no preload and low dose preloads (e.g. ½).

Unidirectional (UD) leakage correction, the [1,1] combination yielded the most accurate CBV estimates with lower error range, with no flip angle dependency For Bidirectional (BD) leakage detection, similar CBV accuracy was achieved with both the [½, ½] and [1,1] dosing schemes, with no flip angle dependency. Bidirectional (BD) leakage detection was found to yield more accurate CBV estimates for the [½, ½] dosing scheme as compared to BW. For the [1,1] dosing scheme, mean CBV accuracy was similar for both approaches, but the error range for Unidirectional (UD) leakage correction (−20% to 20%) was smaller than for BD Bidirectional (BD) leakage detection (−30%-30%).

4. Conclusion

By modifying the single-echo DSC-MRI relaxation rate equation, an improved post-processing leakage correction method is provided that accounts for bidirectional contrast agent transport between the intravascular and interstitial spaces that commonly occurs in angiogenic high-grade gliomas, without a substantial increase in post-processing computation time. Test results demonstrate the importance of considering the interstitial washout term, even when modeling the relaxation rate changes during short image acquisitions. For instance, significant differences were observed between the Bidirectional-model and Unidirectional-model fits to relaxation rate data in high-grade gliomas as early as 10-20 seconds after injection. Furthermore, by including a washout term, the Bidirectional-model alleviates the error in relaxation rate estimates for arteries and normal brain introduced by conventional models constrained to increasing contrast agent concentration over time in all tissues.

By adding one free parameter related to bidirectional transvascular contrast agent exchange, the Bidirectional-model can more accurately determine leakage-corrected rCBV for high-grade gliomas possessing a much greater variety of contrast agent washout dynamics, and better adapt to tissues with greatly disparate washout rates including different tumor types, arteries, and normal appearing white matter. By adding one degree of freedom to the model for $\Delta \hat{R}^*_2(t)$, the Bidirectional-model outperforms the Unidirectional-model in an information content sense as evidenced by superior AIC on average in all whole-brain and contrast-enhancing tumor voxels for the 21 GBM patients in Group 1.

Moreover, in human GBM data, the systems and methods of the present description are able to more closely fit the DSC data compared with the conventional model, with the added benefit that the concentration curves of contrast agent present in the tissue more closely follow the shape of the curves expected on DCE-MRI. Furthermore, the $k_{ep}$ values computed by the Bidirectional-model have a strong correlation with the DCE-derived $k_{ep}$ values. Finally, Bidirectional-model corrected rCBV estimates were often >20% different from Unidirectional-model corrected rCBV estimates, suggesting differences in rCBV between the models may be substantial enough to influence clinical decision-making.

Test results suggest that the conventional Unidirectional-model undercorrects rCBV, with insufficiently increased and decreased rCBV compared to uncorrected rCBV in T1-dominant and T2*-dominant leakage scenarios, respectively. Furthermore, since the low flip angle DSC-MRI protocol for Group 1 patients was largely T2*-dominant, and the largest discrepancies between Bidirectional-model and Unidirectional-model estimates of rCBV existed for T2* dominant voxels, the results suggest that the Bidirectional-model may be particularly advantageous over the Unidirectional-model for correcting the residual T2* effects frequently encountered in dual-echo gradient-echo acquisitions.

Results show that inclusion of bidirectional exchange in leakage correction models for single-echo DSC-MRI, as provided in the systems and methods of the present description, improves the model fit to leakage-contaminated DSC-MRI data and significantly improves estimation of rCBV in high-grade gliomas.

Furthermore, the bidirectional leakage correction method of the present description accounts for backward flux of contrast agent and was shown to reduce rCBV error compared to the unidirectional leakage correction in all 180 acquisition scenarios tested.

It was found that if the computed leakage term does not include back flux of contrast agent, it can cause the corrected ΔR2*(t) curve to adopt a shape noticeably different than Cp (EQ. 12), thereby overestimating and underestimating the "ground truth" curve immediately following the first pass of the bolus. This results in rCBV estimates obtained using the unidirectional algorithm having approximately twice the error compared to estimates obtained using the bidirectional leakage correction algorithm.

In summary, the systems and methods of the present description provide more accurate correction for the T1 or T2* enhancement arising from contrast agent extravasation due to blood-brain barrier disruption in high-grade gliomas by incorporating interstitial washout rates into the DSC-MRI relaxation rate model. To this end, the systems and methods of the present description provide improved patient diagnosis and evaluation of treatment response by more accurately estimating rCBV in DSC-MRI.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic.

As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. An apparatus for performing leakage correction during magnetic resonance imaging of a target anatomy, the method comprising: (a) a computer processor; and (b) a non-transitory computer-readable memory storing instructions executable by the computer processor; (c) wherein said instructions, when executed by the computer processor, perform steps comprising: (i) injecting a Magnetic Resonance (MR) contrast agent into a patient for delivery to target anatomy; (ii) acquiring a dynamic series of T2*-weighted MR images of the target anatomy; and (iii) transforming the dynamic series of T2*-weighted MR images of the target anatomy into blood volume or blood flow images; (iv) wherein said transformation comprises post-processing leakage correction to account for bidirectional contrast agent exchange between intravascular and extravascular spaces.

2. The apparatus of any preceding embodiment, wherein the post-processing leakage correction accounts for contrast agent reflux from an interstitial space back to blood plasma associated with the target anatomy.

3. The apparatus of any preceding embodiment, wherein the dynamic series of T2*-weighted MR images comprise dynamic susceptibility contrast MRI (DSC-MRI) images; and wherein the post-processing leakage correction accounts for interstitial washout rate for the DSC-MRI images.

4. The apparatus of any preceding embodiment, wherein the wherein the post-processing leakage correction calculates leakage corrected relative cerebral blood volume, ($rCBV_{corr}$).

5. The apparatus of any preceding embodiment, wherein leakage corrected relative cerebral blood volume, $rCBV_{corr}$, is calculated according to the equation: $rCBV_{corr} = rCBV + K_2 \int_0^{T} \int_0^{t} \Delta \overline{R}^*_2 (\tau) \cdot e^{-k_{ep}(t-\tau)} d\tau dt$; wherein rCBV is relative cerebral blood volume, and $k_{ep}$ is a transfer coefficient having a non-zero value for extravascular to intravascular contrast flux, $\Delta \overline{R}^*_2(t)$ is whole brain average signal, and $K_2$ is a free parameter related to vascular permeability.

6. The apparatus of any preceding embodiment, wherein said transformation comprises calculating a corrected relaxation rate-time curve according to the equation: $\Delta \hat{R}^*_2(t) = (K_2 + k_{ep} \cdot K_1) \int_0^{t_k} \Delta \overline{R}^*_2(\tau) d\tau - k_{ep} \int_0^{t_k} \Delta \hat{R}^*_2(\tau) d\tau + K_1 \cdot \Delta \overline{R}^*_2(t)$; wherein $\Delta \overline{R}^*_2(t)$ is whole brain average signal, $K_1$ and $K_2$ are free parameters related to vascular permeability, $k_{ep}$ is a transfer coefficient having a non-zero value for extravascular to intravascular contrast flux.

7. The apparatus of any preceding embodiment, wherein the leakage corrected relative cerebral blood volume is calculated as a function of an integral of the corrected relaxation rate-time curve.

8. The apparatus of any preceding embodiment, wherein said transformation is configured to simultaneously calculate leakage corrected relative cerebral blood volume data while simultaneously calculating one or more parameters pertaining to dynamic contrast enhancement (DCE) MRI, without using a separate injection or scan of the target anatomy.

9. The apparatus of any preceding embodiment, wherein the one or more parameters pertaining to the DCE-MRI comprise parameters relating to vascular permeability.

10. The apparatus of any preceding embodiment, wherein said transformation is configured to simultaneously calculate rCBV$_{corr}$, and a transfer coefficient relating to vascular permeability via a single MRI acquisition.

11. A method for performing leakage correction during magnetic resonance imaging, the method comprising: (a) injecting a Magnetic Resonance (MR) contrast agent into a patient for delivery to target anatomy; (b) acquiring a dynamic series of T2*-weighted MR images of the target anatomy; and (c)transforming the dynamic series of T2*-weighted MR images of the target anatomy into blood volume or blood flow images; (d) wherein said transformation comprises post-processing leakage correction to account for bidirectional contrast agent exchange between intravascular and extravascular spaces; and (e) wherein said method is performed by executing instructions on at least one computer processor, said instructions residing in a readable by the computer processor.

12. The method of any preceding embodiment, wherein the post-processing leakage correction accounts for contrast agent reflux from an interstitial space back to blood plasma associated with the target anatomy.

13. The method of any preceding embodiment: wherein the dynamic series of T2*-weighted MR images comprise dynamic susceptibility contrast MRI (DSC-MRI) images; and wherein the post-processing leakage correction accounts for interstitial washout rate for the DSC-MRI images.

14. The method of any preceding embodiment, wherein the wherein the post-processing leakage correction calculates leakage corrected relative cerebral blood volume, (rCBV$_{corr}$).

15. The method of any preceding embodiment, wherein leakage corrected relative cerebral blood volume, rCBV$_{corr}$, is calculated according to the equation: rCBV$_{corr}$=rCBV+ $K_2 \int_0^T \int_0^t \Delta \overline{R}^*_2(\tau) \cdot e^{-k_{ep}(t-\tau)} d\tau dt$; wherein rCBV is relative cerebral blood volume, and k$_{ep}$ is a transfer coefficient having a non-zero value for extravascular to intravascular contrast flux, $\Delta \overline{R}^*_2(t)$ is whole brain average signal and K$_2$ is a free parameter related to vascular permeability.

16. The method of any preceding embodiment, wherein said transformation comprises calculating a corrected relaxation rate-time curve according to the equation: $\Delta \hat{R}^*_2(t)=$ $(K_2+k_{ep} \cdot K_1) \int_0^{t_k} \Delta \overline{R}^*_2(\tau)d\tau - k_{ep} \int_0^{t_k} \Delta \hat{R}^*_2(\tau) d\tau + K_1 \cdot \Delta \overline{R}^*_2(t)$; wherein $\Delta \overline{R}^*_2(t)$ is whole brain average signal, K$_1$ and K$_2$ are free parameters related to vascular permeability, k$_{ep}$ is a transfer coefficient having a non-zero value for extravascular to intravascular contrast flux.

17. The method of any preceding embodiment, wherein the leakage corrected relative cerebral blood volume is calculated as a function of an integral of the corrected relaxation rate-time curve.

18. The method of any preceding embodiment, wherein said transformation is configured to simultaneously calculate leakage corrected relative cerebral blood volume data while simultaneously calculating one or more parameters pertaining to dynamic contrast enhancement (DCE) MRI, without using a separate injection or scan of the target anatomy.

19. The method of any preceding embodiment, wherein the one or more parameters pertaining to the DCE-MRI comprise parameters relating to vascular permeability.

20. The method of any preceding embodiment, wherein said transformation is configured to simultaneously calculate rCBV$_{corr}$, and a transfer coefficient relating to vascular permeability via a single MRI acquisition.

21. A system for performing leakage correction during magnetic resonance imaging of a target anatomy, the method comprising: (a) an MRI scanner configured for scanning the target anatomy; (b) a computer processor coupled to the MRI scanner; and (c) a non-transitory computer-readable memory storing instructions executable by the computer processor; (d) wherein said instructions, when executed by the computer processor, perform steps comprising: (i) injecting a Magnetic Resonance (MR) contrast agent into a patient for delivery to target anatomy; (ii) acquiring a dynamic series of T2*-weighted MR images of the target anatomy; and (iii) transforming the dynamic series of T2*-weighted MR images of the target anatomy into blood volume or blood flow images; (iv) wherein said transformation comprises post-processing leakage correction to account for bidirectional contrast agent exchange between intravascular and extravascular spaces.

22. The system of any preceding embodiment, wherein the post-processing leakage correction accounts for contrast agent reflux from an interstitial space back to blood plasma associated with the target anatomy.

23. The system of any preceding embodiment: wherein the dynamic series of T2*-weighted MR images comprise dynamic susceptibility contrast MRI (DSC-MRI) images; and wherein the post-processing leakage correction accounts for interstitial washout rate for the DSC-MRI images.

24. The system of any preceding embodiment, wherein the wherein the post-processing leakage correction calculates leakage corrected relative cerebral blood volume, (rCBV$_{corr}$).

25. The system of any preceding embodiment, wherein leakage corrected relative cerebral blood volume, rCBV$_{corr}$, is calculated according to the equation: rCBV$_{corr}$=rCBV+ $K_2 \int_0^T \int_0^t \Delta \overline{R}^*_2(\tau) \cdot e^{-k_{ep}(t-\tau)} d\tau dt$; wherein rCBV is relative cerebral blood volume, and k$_{ep}$ is a transfer coefficient having a non-zero value for extravascular to intravascular contrast flux, $\Delta \overline{R}^*_2(t)$ is whole brain average signal and K$_2$ is a free parameter related to vascular permeability.

26. The system of any preceding embodiment, wherein said transformation comprises calculating a corrected relaxation rate-time curve according to the equation: $\Delta \hat{R}^*_2(t)=$ $(K_2+k_{ep} \cdot K_1) \int_0^{t_k} \Delta \overline{R}^*_2(\tau)d\tau - k_{ep} \int_0^{t_k} \Delta \hat{R}^*_2(\tau) d\tau + K_1 \cdot \Delta \overline{R}^*_2(t)$; wherein $\Delta \overline{R}^*_2(t)$ is whole brain average signal, K$_1$ and K$_2$ are free parameters related to vascular permeability, k$_{ep}$ is a transfer coefficient having a non-zero value for extravascular to intravascular contrast flux.

27. The system of any preceding embodiment, wherein the leakage corrected relative cerebral blood volume is calculated as a function of an integral of the corrected relaxation rate-time curve.

28. The system of any preceding embodiment, wherein said transformation is configured to simultaneously calculate leakage corrected relative cerebral blood volume data while simultaneously calculating one or more parameters pertaining to dynamic contrast enhancement (DCE) MRI, without using a separate injection or scan of the target anatomy.

29. The system of any preceding embodiment, wherein the one or more parameters pertaining to the DCE-MRI comprise parameters relating to vascular permeability.

30. The system of any preceding embodiment, wherein said transformation is configured to simultaneously calculate $rCBV_{corr}$, and a transfer coefficient relating to vascular permeability via a single MRI acquisition.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

```
%rCBV_Correction
%Corrects rCBV using linear original Tofts, nonlinear original Tofts, and
%nonlinear extended Tofts
%constants
%tmin = 26; %last time point for establishing baseline signal
late_tp = 9; %number of time points taken to eliminate leaky voxels
%TE = 32 * 10^-3; %s
%time_res = 1.8; %s (time resolution)
%load mask, dsc, grab dsc size
mask = load_untouch_nii('brain.nii.gz'); %derived from bet2
%change mask to 64-bit
mask.hdr.dime.datatype = 64;
mask.hdr.dime.bitpix = 64;
dsc = load_untouch_nii('DSC.nii.gz');
[xmax,ymax,zmax,tmax] = size(dsc.img);
dsc.img = repmat(double(mask.img),[1 1 1 tmax]).*double(dsc.img);
%convert dsc signal to class double
t = (0:tmax-tmin)*time_res;
%
%calculate whole-brain average
%
%use first tmin (default: 25) time points to establish baseline signal
early_sig = dsc.img(:,:,:,1:tmin);
S0 = median(early_sig,4); %take median of tp for baseline signal
%calculate signal, take mean, std
S = -log(double(dsc.img)./repmat(S0,[1 1 1 tmax]))./TE;
new_S = dsc;
new_S.img = S;
new_S.hdr.dime.bitpix = 64;
new_S.hdr.dime.datatype = 64;
%save_untouch_nii(new_S,'R2.nii.gz');
S(S == Inf) = 0; %convert Inf to NaN
S(isnan(S)) = 0;
S(S == -Inf) = 0;
early_sig = S(:,:,:,1:tmin);
sd_early_sig = std(early_sig,[ ],4);
mean_early_sig = mean(early_sig,4);
```

TABLE 1-continued

```
late_sig = S(:,:,:,tmax-late_tp:tmax);
late_sig_enh = mean(late_sig,4);
thresh_S = mean_early_sig + sd_early_sig;
low_thresh_S = mean_early_sig - sd_early_sig;
%eliminate voxels with signal intensity <1 SD
nonleak_vox = (late_sig_enh < thresh_S) & (late_sig_enh > low_thresh_S);
nonleak_vox_time = repmat(nonleak_vox,[1 1 1 tmax]);
sig_nonleak = S.*nonleak_vox_time; %use voxels with only low-to-no signal enhancement
whole_brain_avg = squeeze(nanmean(nanmean(nanmean(sig_nonleak,3),2),1));
%signal proportional to AIF
csvwrite('wba.csv',whole_brain_avg);
%allocate matrices
rCBV_final = zeros(xmax,ymax,zmax);
%3 parameter LLSQ (murase et al, efficient aif, mrm, 2004)
X1 = cumsum(whole_brain_avg(tmin:tmax));
col1 = whole_brain_avg(tmin:tmax); %whole brain avg vector
%tic;
for i = 1:numel(mask_vox)
    sprintf('%d out of %d',i,numel(mask_vox))
    [a,b,c] = ind2sub([xmax,ymax,zmax],mask_vox(i));
    uncorr_sig = squeeze(S(a,b,c,tmin:tmax)); %uncorrected signal vector
    uncorr_sig(uncorr_sig == Inf) = 0;
    %3 parameter LLSQ
    X2 = -cumsum(uncorr_sig);
    X = [X1 X2 whole_brain_avg(tmin:tmax)];
    Y = X\uncorr_sig;
    correction = X(:,1:2)*Y(1:2);
    corr_sig = uncorr_sig - correction;
    rCBV_final(a,b,c) = trapz(corr_sig)*time_res;
end
%save NLSQ correction (addition of kep)
mask.img = rCBV_final;
save_untouch_nii(mask,'final.rCBV.map.nii.gz');
```

TABLE 2

| Flip Angle (degrees) | TE (ms) | TR (s) | Preload Dosage | Mean Uncorrected Error (%) | Mean Bidirectional Error (%) |
|---|---|---|---|---|---|
| 35 | 35 | 1.5 | None | 67.4 | 2.47 |
| 35 | 25 | 1.5 | ¼ | 63.3 | 2.25 |
| 60 | 45 | 2.0 | ¼ | 49.7 | 2.25 |
| 60 | 55 | 1.5 | ¼ | 44.4 | 2.32 |
| 35 | 15 | 2.0 | ¼ | 56.3 | 2.45 |
| 35 | 35 | 1.0 | ¼ | 56.9 | 2.46 |
| 60 | 35 | 2.0 | ½ | 64.6 | 2.32 |
| 60 | 45 | 1.5 | ½ | 56.7 | 2.44 |
| 35 | 15 | 2.0 | ½ | 56.3 | 2.45 |
| 60 | 35 | 1.0 | 1 | 55.2 | 2.01 |
| 90 | 15 | 1.0 | 1 | 60.1 | 2.06 |
| 90 | 55 | 1.0 | 1 | 47.8 | 2.08 |
| 90 | 45 | 1.5 | 1 | 64.5 | 2.08 |
| 60 | 25 | 1.5 | 1 | 66.9 | 2.12 |
| 60 | 15 | 2 | 1 | 67.5 | 2.26 |
| 60 | 45 | 1 | 1 | 71.3 | 2.29 |
| 90 | 35 | 1.5 | 1 | 49.7 | 2.30 |
| 90 | 25 | 2 | 1 | 59.3 | 2.37 |
| 90 | 35 | 2 | 1 | 77.7 | 2.38 |
| 90 | 55 | 1.5 | 1 | 76.6 | 2.38 |

What is claimed is:

1. An apparatus for performing leakage correction during magnetic resonance imaging of a target anatomy, the apparatus comprising:
   (a) a computer processor; and
   (b) a non-transitory computer-readable memory storing instructions executable by the computer processor;
   (c) wherein the computer processor is programmed to execute said instructions to perform steps comprising:
      (i) controlling injecting of a Magnetic Resonance (MR) contrast agent into a patient for delivery to target anatomy;

(ii) acquiring a dynamic series of T2*-weighted MR images of the target anatomy; and (iii) transforming, using a bidirectional model, the dynamic series of T2*-weighted MR images of the target anatomy into blood volume or blood flow images;

(iv) wherein said bidirectional model accounts for bidirectional contrast agent exchange between intravascular and extravascular spaces.

2. The apparatus of claim 1, wherein the computer processor is further programmed to use the bidirectional model to account for contrast agent reflux from an interstitial space back to blood plasma associated with the target anatomy.

3. The apparatus of claim 1, wherein the computer processor is further programmed to:
acquire the dynamic series of T2*-weighted MR images to comprise dynamic susceptibility contrast MRI (DSC-MRI) images; and
use the bidirectional model to account for interstitial washout rate for the DSC-MRI images.

4. The apparatus of claim 3, wherein the computer processor is further programmed to use the bidirectional model to calculate leakage corrected relative cerebral blood volume, ($rCBV_{corr}$).

5. The apparatus of claim 4, wherein the computer processor is further programmed to calculate the leakage corrected relative cerebral blood volume, $rCBV_{corr}$, according to an equation:

$$rCBV_{corr} = rCBV + K_2 \int_0^T \int_0^t \Delta \overline{R}_2^*(\tau) \square e^{-k_{ep}(t-\tau)} d\tau dt$$

wherein rCBV is relative cerebral blood volume, and $k_{ep}$ is a transfer coefficient having a non-zero value for extravascular to intravascular contrast flux, $\Delta \overline{R}_2^*(\tau)$ is whole brain average signal, and $K_2$ is a free parameter related to vascular permeability.

6. The apparatus of claim 4, wherein the computer processor is further programmed to calculate a corrected relaxation rate-time curve according to an equation:

$$\Delta \hat{R}_2^*(t) = (K_2 + k_{ep} \cdot K_1) \int_0^{tk} \Delta \overline{R}_2^*(\tau) d\tau - k_{ep} \int_0^{tk} \Delta \hat{R}_2^*(\tau) d\tau = K_1 \cdot \Delta \hat{R}_2^*(t)$$

wherein $\Delta \overline{R}_2^*(t)$ is whole brain average signal, $K_1$ and $K_2$ are free parameters related to vascular permeability, $k_{ep}$ is a transfer coefficient having a non-zero value for extravascular to intravascular contrast flux.

7. The apparatus of claim 4, wherein the computer processor is further programmed to calculate the leakage corrected relative cerebral blood volume as a function of an integral of a corrected relaxation rate-time curve.

8. The apparatus of claim 4, wherein the computer processor is further programmed to simultaneously calculate leakage corrected relative cerebral blood volume data while simultaneously calculating one or more parameters pertaining to dynamic contrast enhancement (DCE) MRI, without using a separate injection or scan of the target anatomy.

9. The apparatus of claim 8, wherein the computer processor is further programmed to calculate the one or more parameters pertaining to the DCE-MRI to comprise parameters relating to vascular permeability.

10. The apparatus of claim 8, wherein the computer processor is further programmed to simultaneously calculate $rCBV_{corr}$, and a transfer coefficient relating to vascular permeability via a single MRI acquisition.

11. A method for performing leakage correction during magnetic resonance imaging, the method comprising:
(a) injecting a Magnetic Resonance (MR) contrast agent into a patient for delivery to target anatomy;

(b) acquiring a dynamic series of T2*-weighted MR images of the target anatomy; and (c) transforming the dynamic series of T2*-weighted MR images of the target anatomy into blood volume or blood flow images using a bidirectional model;

(d) wherein said bidirectional model accounts for bidirectional contrast agent exchange between intravascular and extravascular spaces; and (e) wherein said method is performed by executing instructions on at least one computer processor, said instructions residing in a readable by the computer processor.

12. The method of claim 11, wherein the bidirectional model accounts for contrast agent reflux from an interstitial space back to blood plasma associated with the target anatomy.

13. The method of claim 11:
wherein the dynamic series of T2*-weighted MR images comprise dynamic susceptibility contrast MRI (DSC-MRI) images; and
wherein the bidirectional model accounts for interstitial washout rate for the DSC-MRI images.

14. The method of claim 13, wherein the computer processor calculates leakage corrected relative cerebral blood volume, ($rCBV_{corr}$) when executing the instructions.

15. The method of claim 14, wherein leakage corrected relative cerebral blood volume, $rCBV_{corr}$, is calculated according to an equation:

$$rCBV_{corr} = rCBV + K_2 \int_0^T \int_0^t \Delta \overline{R}_2^*(\tau) \cdot e^{-k_{ep}(t-\tau)} d\tau dt$$

wherein rCBV is relative cerebral blood volume, and $k_{ep}$ is a transfer coefficient having a non-zero value for extravascular to intravascular contrast flux, $\Delta \overline{R}_2^*(t)$ is whole brain average signal and $K_2$ is a free parameter related to vascular permeability.

16. The method of claim 14, wherein said transformation comprises calculating a corrected relaxation rate-time curve according to an equation:

$$\Delta \hat{R}_2^*(t) = (K_2 + k_{ep} \cdot K_1) \int_0^{tk} \Delta \overline{R}_2^*(\tau) d\tau - k_{ep} \int_0^{tk} \Delta \hat{R}_2^*(\tau) d\tau = K_1 \cdot \Delta \hat{R}_2^*(t)$$

wherein $\Delta \overline{R}_2^*(t)$ is whole brain average signal, $K_1$ and $K_2$ are free parameters related to vascular permeability, $k_{ep}$ is a transfer coefficient having a non-zero value for extravascular to intravascular contrast flux.

17. The method of claim 14, wherein the leakage corrected relative cerebral blood volume is calculated as a function of an integral of a corrected relaxation rate-time curve.

18. The method of claim 14, wherein said transformation is configured to simultaneously calculate leakage corrected relative cerebral blood volume data while simultaneously calculating one or more parameters pertaining to dynamic contrast enhancement (DCE) MRI, without using a separate injection or scan of the target anatomy.

19. A system for performing leakage correction during magnetic resonance imaging of a target anatomy, the system comprising:
(a) an MRI scanner configured for scanning the target anatomy;
(b) a computer processor coupled to the MRI scanner; and
(c) a non-transitory computer-readable memory storing instructions executable by the computer processor;
(d) wherein said instructions, when executed by the computer processor, the computer processor is configured to perform steps comprising:
(i) injecting a Magnetic Resonance (MR) contrast agent into a patient for delivery to target anatomy;

(ii) acquiring a dynamic series of T2*-weighted MR images of the target anatomy; and
(iii) using a bidirectional model to transform the dynamic series of T2*-weighted MR images of the target anatomy into blood volume or blood flow images;
(iv) wherein said bidirectional model accounts for bidirectional contrast agent exchange between intravascular and extravascular spaces.

20. The system of claim 19, wherein the model accounts for contrast agent reflux from an interstitial space back to blood plasma associated with the target anatomy.

\* \* \* \* \*

UNITED STATES PATENT AND TRADEMARK OFFICE
CERTIFICATE OF CORRECTION

PATENT NO.         : 10,973,433 B2                                Page 1 of 1
APPLICATION NO.    : 15/754237
DATED              : April 13, 2021
INVENTOR(S)        : Benjamin Ellingson et al.

It is certified that error appears in the above-identified patent and that said Letters Patent is hereby corrected as shown below:

In the Specification

Column 3, Line 63, "$\Delta R^*_2(t)$" should read -- $\Delta \hat{R}^*_{2,E}(t)$ --.

Column 6, Eq. 2, "$C_E(t) = k_{trans} \cdot (C_p(t) * e^{-k_{ep}}t)$," should read -- $C_E(t) = k_{trans} \cdot (C_p(t) * e^{-k_{ep}t})$ --.

Column 9, Line 46, "$\Delta \hat{R}_2(t)$" should read -- $\Delta \hat{R}^*_{2,E}(t)$ --.

Column 10, Line 8, "$\Delta \hat{R}^*_2(t)$" should read -- $\Delta \hat{R}^*_{2,E}(t)$ --.

Column 10, Line 16, "$\Delta \hat{R}^*_2(t)$" should read -- $\Delta R^*_{2,E}(t)$ --.

In the Claims

Column 23, Claim 5, Line 30, "$rCBV_{corr} = rCBV + K_2 \int_0^T \int_0^t \Delta \bar{\hat{R}}^*_2(\tau) \square e^{-k_{ep}(t-\tau)} d\tau dt$,"

should read -- $rCBV_{corr} = rCBV + K_2 \int_0^T \int_0^t \Delta \bar{R}^*_2(\tau) \cdot e^{-k_{ep}(t-\tau)} d\tau dt$ --.

Signed and Sealed this
First Day of June, 2021

Drew Hirshfeld
*Performing the Functions and Duties of the
Under Secretary of Commerce for Intellectual Property and
Director of the United States Patent and Trademark Office*